United States Patent
Martin et al.

(10) Patent No.: US 7,258,859 B2
(45) Date of Patent: Aug. 21, 2007

(54) METHOD FOR THE TREATMENT OF MULTIPLE SCLEROSIS

(75) Inventors: Roland Martin, Bethesda, MD (US); Henry McFarland, Gaithersburg, MD (US); Bibiana Bielekova, Kensington, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 528 days.

(21) Appl. No.: 10/607,598

(22) Filed: Jun. 27, 2003

(65) Prior Publication Data

US 2004/0109859 A1 Jun. 10, 2004

Related U.S. Application Data

(60) Provisional application No. 60/393,021, filed on Jun. 28, 2002.

(51) Int. Cl.
*A61K 39/00* (2006.01)
*A61K 38/21* (2006.01)
(52) U.S. Cl. ............... 424/184.1; 424/85.6; 424/143.1
(58) Field of Classification Search ............... None
See application file for complete search history.

(56) References Cited

U.S. PATENT DOCUMENTS

| | | | |
|---|---|---|---|
| 5,530,101 A | 6/1996 | Queen et al. | |
| 5,585,089 A | 12/1996 | Queen et al. | |
| 5,620,686 A | 4/1997 | Mason | |
| 5,693,762 A | 12/1997 | Queen et al. | |
| 5,817,306 A * | 10/1998 | Haskill et al. | 424/85.2 |
| 6,013,256 A | 1/2000 | Light et al. | |
| 6,096,728 A | 8/2000 | Collins et al. | |
| 6,180,370 B1 | 1/2001 | Queen et al. | |
| 6,346,247 B1 | 2/2002 | Stafford et al. | |

FOREIGN PATENT DOCUMENTS

| | | |
|---|---|---|
| WO | WO89/09622 | 10/1989 |
| WO | WO90/07861 | 7/1990 |
| WO | WO92/13886 | 8/1992 |
| WO | WO93/01289 | 1/1993 |
| WO | WO 00/25816 | 5/2000 |

OTHER PUBLICATIONS

Goodin, Therepeutic developments in multiple sclerosis (2000), Exp. Opin. Invest. Drugs, vol. 9(4), pp. 655-670.*
"Advances in Basic and Clinical Research on MS Reported at AAN," www.nationalmssociety.org/Research-2003Apr15.asp, Apr. 15, 2003.
Bellamy et al., "The distribution of interleukin-2 receptor bearing lymphocytes in multiple sclerosis: evidence for a key role of activated lymphocytes," *Clin. Exp. Immunol.*61: 248-256, 1985.
Brown et al., "Anti-Tac-H, a humanized antibody to the interleukin 2 receptor, prolongs primate cardiac allograft survival," *Proc. Natl. Acad. Sci. USA* 88: 2663-2667, 1991.
Church, A., "Clinical advances in therapies targeting the interleukin-2 receptor," *Q J Med* 96: 91-102, 2003.
Giorelli et al., "IFN-β1a Modulates the Expression of CTLA-4 and CD28 Splice Variants in Human Mononuclear Cells: Induction of Soluble Isoforms," *Journal of Interferon and Cytokine Research* 21: 809-812, 2001.
Junghans et al., "Anti-Tac-H, a Humanized Antibody to the Interleukin 2 Receptor with New Features for Immunotherapy in Malignant and Immune Disorders," *Cancer Res.* 50(5): 1495-1502, 1990.
Khoury et al., "Changes in Activated T Cells in the Blood Correlate with Disease Activity in Multiple Sclerosis," *Arch. Neurol* 57: 1183-1189, 2000.
Lee et al., "Spatial mapping of $T_2$ and gadolinium-enhancing $T_1$ lesion volumes in multiple sclerosis: evidence for distinct mechanisms of lesion genesis?" *Brain* 122: 1261-1270, 1999.
Lehky et al., "Reduction in HTLV-I Proviral Load and Spontaneous Lymphoproliferation in HTLV-I-Associated Myelopathy/Tropical Spastic Paraparesis Patients Treated with Humanized Anti-Tac," *Annals of Neurology* 44: 942-947, 1998.
Marwick, C., "Scientists Recall Progress and Promise of Translational Research," *J. Natl. Cancer Inst.* 93: 13-15, 2001.
"Monoclonal antibodies with clinical indications," www/imgt. cines.fr:8104/textes/IMGTrepertoire/GenesClinical/monoclonalantibodies, May 19, 2003.
Nussenblatt et al., "Treatment of noninfectious intermediate and posterior uveitis with the humanized anti-Tac mAb: A phase I/II clinical trial," *Proc. Natl. Acad. Sci. USA* 96 (13): 7462-7466, 1999.
Package insert for Rebif (interferon beta-1a), Nov. 6, 2002.
Package insert for Zenapax (Daclizumab), Dec. 1997.
Paty et al., "Interferon beta-1b is effective in relapsing-remitting multiple sclerosis," *Neurology* 43:662-667.
Posey et al., "TCP presents its annual list of drugs in development and what their approval will mean to long-term care patients," www.ascp.com/public/pubs/tcp/1997/apr/newdrugs.html, Jun. 4, 2002.
Queen et al., "A humanized antibody that binds to the interleukin 2 receptor," *Proc. Natl. Acad. Sci. USA* 86 (24): 10029-10033, 1989.
Samkoff, Lawrence, "Multiple Sclerosis: Update of Treatment," *Hospital Physician* pp. 21-27, 2002.

(Continued)

*Primary Examiner*—Christine J. Saoud
*Assistant Examiner*—Jegatheesan Seharaseyon
(74) *Attorney, Agent, or Firm*—Klarquist Sparkman LLP

(57) ABSTRACT

A method for treating a subject with multiple sclerosis is disclosed herein. In one embodiment, a method is provided for treating a subject with multiple sclerosis that includes administering to the subject a therapeutically effective amount of an IL-21 receptor antagonist, wherein the subject has failed to respond treatment with beta interferon, thereby treating the subject.

17 Claims, 9 Drawing Sheets

OTHER PUBLICATIONS

"Study of Zenapax in the treatment of multiple sclerosis," www.mult.sclerosis.org/news/Nov2000/ZenapaxMS.html, Nov. 27, 2000.

Waldmann, et al., "Emerging Therapies: Spectrum of Applications of Monoclonal Antibody Therapy," *Hematology* (1): 394, 2000.

Wandinger et al., "Complex Immunomodulatory Effects of Interferon-beta in Multiple Sclerosis Include the Upregulation of T Helper 1-associated Marker Genes," *Ann. Neurol.*, 50(3):349-57 (2001).

Nussenblatt et al., *Proc. Natl. Acad. Sci. USA*, 96:7462-7466, 1999.

Patti et al., *Acta Neurol. Scand.*, 100:283-289, 1999.

Becker et al. "Differential Gene Expression in Multiple Sclerosis Lesions Identified Using cDNA Microarrays," *Poster Abstracts / J. Neuroimmunology* 90:71 (1998) *Abstract only*.

Sharief et al. "Reduced expression of the inhibitor of apoptosis proteins in T cells from patients with multiple sclerosis following interferon-β therapy," *J. Neuroimmunology* 129:224-231 (2002).

Bielekova et al., "Daclizumab Inhibits Inflammation and Stabilizes Disease Progression in MS," *Short Communication—Annals of Neurology*, 17 pages, Aug. 14, 2006.

Bielekova et al., "Humanized anti-CD25 (daclizumab) inihibits disease activity in multiple sclerosis patients failing to respond to interferon {beta}," *PNAS* 101(23):8705-8708 (Jun. 8, 2004).

Bielekova et al., "Regulatory CD56bright natural killer cells mediate immunomodulatory effects of IL-2R {alpha}-targeted therapy (daclizumab) in multiple sclerosis," *PNAS* 103(15):5941-5946 (Apr. 11, 2006).

Rose et al., "Treatment of Multiple Sclerosis with an Anti-Interleukin-2 Receptor Monoclonal Antibody," *Ann Neurol* 56:864-867 (2004).

Paty et al., "Interferon beta-1b is effective in relapsing-remitting multiple sclerosis," *Neurology* 43:662-667, 1993.

\* cited by examiner

METHOD FOR THE TREATMENT OF MULTIPLE SCLEROSIS

PRIORITY CLAIM

Priority is claimed to PCT Application No. PCT/US02/38290, filed Nov. 27, 2002, which claims the benefit of U.S. Provisional Application No. 60/393,021, filed Jun. 28, 2002, both of which are incorporated by reference in their entirety.

FIELD

This disclosure relates to the treatment of autoimmune diseases, specifically to the treatment of multiple sclerosis using an antagonist of the IL-2 receptor, such as an antibody that binds the IL-2 receptor (IL-2R).

BACKGROUND

Multiple sclerosis (MS) is a chronic, neurological, autoimmune, demyelinating disease. MS can cause blurred vision, unilateral vision loss (optic neuritis), loss of balance, poor coordination, slurred speech, tremors, numbness, extreme fatigue, changes in intellectual function (such as memory and concentration), muscular weakness, paresthesias, and blindness. Many subjects develop chronic progressive disabilities, but long periods of clinical stability may interrupt periods of deterioration. Neurological deficits may be permanent or evanescent. In the United States there are about 250,000 to 400,000 persons with MS, and every week about 200 new cases are diagnosed. Worldwide, MS may affect 2.5 million individuals. Because it is not contagious, which would require U.S. physicians to report new cases, and because symptoms can be difficult to detect, the incidence of disease is only estimated and the actual number of persons with MS could be much higher.

The pathology of MS is characterized by an abnormal immune response directed against the central nervous system. In particular, T-lymphocytes are activated against the myelin sheath of the neurons of the central nervous system causing demyelination. In the demyelination process, myelin is destroyed and replaced by scars of hardened "sclerotic" tissue which is known as plaque. These lesions appear in scattered locations throughout the brain, optic nerve, and spinal cord. Demyelination interferes with conduction of nerve impulses, which produces the symptoms of multiple sclerosis. Most subjects recover clinically from individual bouts of demyelination, producing the classic remitting and exacerbating course of the most common form of the disease known as relapsing-remitting multiple sclerosis.

MS develops in genetically predisposed individuals and is most likely triggered by environmental agents such as viruses (Martin et al., *Ann. Rev. Immunol.* 10:153-187, 1992). According to current hypotheses, activated autoreactive CD4+ T helper cells (Th1 cells) which preferentially secrete interferon-gamma (IFN-γ) and tumor necrosis factors alpha/beta (TNF-α/β), induce inflammation and demyelination in MS (Martin et al., supra). Available data suggest that the predisposition to mount a Th1-like response to a number of different antigens is an important aspect of MS disease pathogenesis. Proinflammatory cytokines (such as IFN-γ, TNF-α/β) and chemokines secreted by Th1 cells contribute to many aspects of lesion development including opening of the blood-brain-barrier, recruitment of other inflammatory cells, activation of resident glia (micro- and astroglia) and the effector phase of myelin damage via nitrogen and oxygen radicals secreted by activated macrophages (Wekerle et al., *Trends Neuro Sci.* 9:271-277, 1986) (Martin et al., supra).

The peripheral activation of autoreactive lymphocytes via molecular mimicry (Wucherpfennig and Strominger, *Cell.* 80:695-705, 1995; Gran et al., *Ann. Neurol.* 45:559-567, 1999) is a critical prerequisite for T cell migration into the CNS compartment (Calabresi et al., *Ann. Neurol.* 41:669-674, 1998). Only activated T cells expressing the necessary adhesion molecules are able to migrate across the blood-brain-barrier. It has been hypothesized that T lymphocytes in MS patients as well as in models for MS such as experimental allergic encephalomyelitis (EAE; in particular in SJL mice, see Encinas et al. *Nature Genet.* 21:158-160, 1999) differ from non-susceptible individuals by being in a different state of activation (Calabresi et al., supra), as the cells enter the cell-cycle more readily, stay longer in growth phase, may exhibit defects in apoptosis pathways (Zipp et al., *Ann. Neurol.* 43:116-120, 1998), or are in vivo activated as indicated by higher mutation rates in the hypoxanthine-phosphoribosyl transferase gene in myelin-specific T cells (Allegretta et al., *Science.* 247:718-721, 1990).

The status of MS patients can be evaluated by longitudinal, monthly follow-up of magnetic resonance (MRI) activity in the brain of MS patients. MRI offers a unique set of outcome measures for phase I/II clinical trials in small cohorts of patients, and is thus well suited to establish data for proof of principle for novel therapeutic strategies (e.g., see Harris et al., *Ann. Neurol.* 29:548-555, 1991; MacFarland et al., *Ann. Neurol.* 32:758-766, 1992; Stone et al., *Ann. Neurol.* 37:611-619, 1995). There are currently four approved treatments for relapsing-remitting MS, three types of IFN-β (the Interferon-B multiple sclerosis study group, *Neurology.* 43:655-661, 1993; the IFNB Multiple Sclerosis Study Group and the University of British Columbia MS/MRI Analysis Group, *Neurology.* 45:1277-1285, 1995; Jacobs et al., *Ann. Neurol.* 39:285-294, 1996), and copolymer-1 (Johnson K P, Group. tCMST, *J. Neurol.* 242:S38, 1995). Treatment failures have been linked to the development of neutralizing anti-IFN-β antibodies, although their role is also not completely understood at present (the IFNB Multiple Sclerosis Study Group and the University of British Columbia MS/MRI Analysis Group, *Neurology.* 47:889-894, 1996). Failure to respond to IFN-β is not a rare event, and therefore it is important to identify suitable combinations of standard IFN-β therapy with other treatment modalities, and new therapeutic protocols.

SUMMARY

Methods are disclosed herein for treating a subject, such as a human subject, with multiple sclerosis.

In one embodiment, the method includes administering to the subject a therapeutically effective amount of an IL-2 receptor (IL-2R) antagonist in the absence of treatment with beta interferon, thereby ameliorating a symptom or symptoms of multiple sclerosis and treating the subject. In one example, the subject has failed to respond to previous treatment with beta interferon. In another example, the IL-2R antagonist is a monoclonal antibody, such as a chimeric, humanized or human antibody, that specifically binds to the α or p55 (Tac) chain of the IL-2 receptor.

In another embodiment, a method is provided for treating a subject with multiple sclerosis, wherein the method includes administering a therapeutically effective amount of an antibody, such as a chimeric, humanized, or fully human monoclonal antibody that specifically binds the interleukin-2 receptor. The monoclonal antibody is administered at least biweekly for a period of at least two months. The subject is not treated with interferon-β during the administration of the monoclonal antibody. In one example, the monoclonal antibody binds p55. In another specific non-limiting example, the subject has previously failed to respond to treatment with interferon-β.

In a further embodiment, a method of treatment is disclosed in which administration of interferon-beta is combined with administration of an antagonist of the IL-2R to provide significant clinical improvement in individuals with MS. In particular examples, the IL-2R antagonist is an antibody, such as a monoclonal antibody, for example an anti-p55 antibody, such as daclizumab.

The foregoing and other features and advantages will become more apparent from the following detailed description of several embodiments, which proceeds with reference to the accompanying figures.

DETAILED DESCRIPTION

Figure 1:
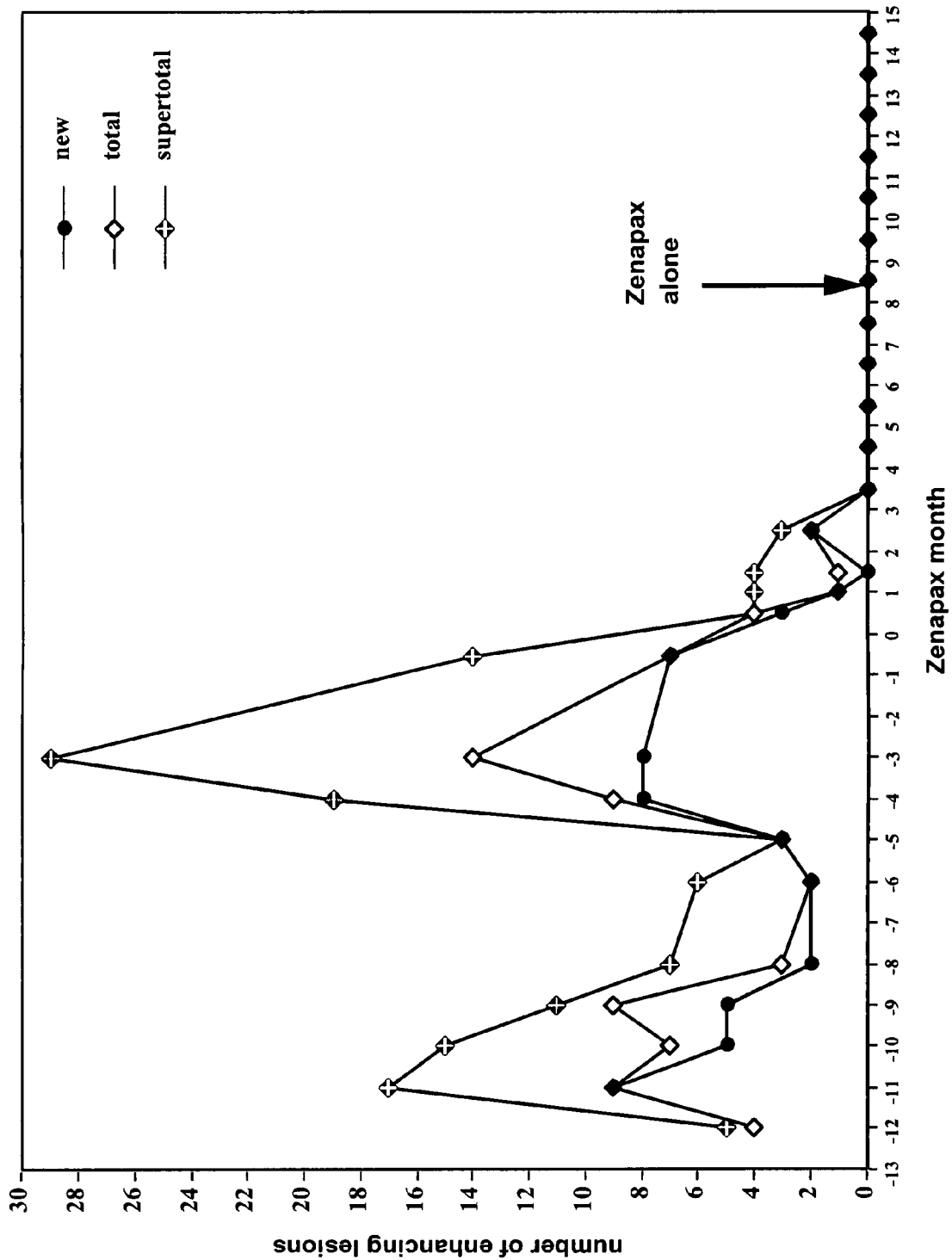
FIG. 1 is a graph of the number of new, total, supertotal and T2LL lesions in a subject treated with Zenapax® alone over time. The subject did not respond to previous combination therapy with Zenapax® and interferon (IFN) beta, as indicated in the region to the right of the solid vertical line. Initiation of Zenapax® monotherapy (in the absence of treatment with interferon-beta) is shown by the arrow. No new lesions were detected following the initiation of Zenapax® monotherapy.

I. Abbreviations
    CDR: complementarity determining region
    CBC: complete blood count
    CNP: Cyclic nucleotide 3'-phosphodiesterase
    EDSS: expanded disability status scale
    FR: framework region
    Gd: gadolinium
    HIV: human immunodeficiency virus
    HV: hypervariable region
    IFN: interferon
    Ig: immunoglobulin
    IL-2: interleukin 2
    IL-2R: interleukin 2 receptor
    kg: kilogram
    KLH: keyhole limpet hemocyanin
    LPS: lippopolysaccharide
    MBP: myelin basic protein
    mg: milligram
    mm: millimeter
    MOG: myelin/oligodendrocyte glycoprotein
    MRI: magnetic resonance imaging
    MS: multiple sclerosis
    NK: natural killer
    NO-: nitric oxide
    PBMC: peripheral blood mononuclear cells
    PLP: myelin proteolipid protein
    SRS: Scripps Neurological Rating Scale
    TGF: transforming growth factor
    TNF: tumor necrosis factor
    VH: variable heavy
    VL: variable light II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Definitions and additional information known to one of skill in the art in immunology can be found, for example, in *Fundamental Immunology*, W. E. Paul, ed., fourth edition, Lippincott-Raven Publishers, 1999.

In order to facilitate review of the various embodiments of this disclosure, the following explanations of specific terms are provided:

Adverse Effects: Any undesirable signs, including the clinical manifestations of abnormal laboratory results, or medical diagnoses noted by medical personnel, or symptoms reported by the subject that have worsened. Adverse events include, but are not limited to, life-threatening events, an event that prolongs hospitalization, or an event that results in medical or surgical intervention to prevent an undesirable outcome.

Antagonist of an IL-2 Receptor (IL-2R): An agent that specifically binds to the IL-2R, or a component thereof, and inhibits a biological function of the IL-2 receptor or the component. Exemplary functions that can be inhibited are the binding of IL-2 to the IL-2R, the intracellular transmission of a signal from binding of IL-2, and proliferation and/or activation of lymphocytes such as T cells in response to IL-2. In one embodiment, IL-2R antagonists of use in the methods disclosed herein inhibit at least one of these functions. Alternatively, IL-2R antagonist of use in the methods disclosed herein can inhibit more than one or all of these functions.

In one example, an IL-2 receptor antagonist is an antibody that specifically binds Tac (p55), such as Zenapax® (see below). Other anti-p55 agents include the chimeric antibody basiliximab (Simulect®), BT563 (see Baan et al., *Transplant. Proc.* 33:224-2246, 2001), and 7G8. Basiliximab has been reported to be beneficial in preventing allograft rejection (Kahan et al., *Transplantation* 67:276-84,1999), and treating psoriasis (Owen & Harrison, *Clin. Exp. Dermatol.* 25:195-7, 2000). An exemplary human anti-p55 antibody of use in the methods of the invention is HuMax-TAC, being developed by Genmab. In another example, an IL-2 receptor antagonist is an antibody that specifically binds the p75 or β subunit of the IL-2R.

Additional antibodies that specifically bind the IL-2 receptor are known in the art. For example, see U.S. Pat. No. 5,011,684; U.S. Pat. No.5,152,980; U.S. Pat. No. 5,336,489; U.S. Pat. No. 5,510,105; U.S. Pat. No. 5,571,507; U.S. Pat. No. 5,587,162; U.S. Pat. No. 5,607,675; U.S. Pat. No. 5,674,494; U.S. Pat. No. 5,916,559. The mik-β1 antibody is an antagonist that specifically binds the beta chain of human IL-2R.

In another example, an IL-2 receptor antagonist is a peptide antagonist that is not an antibody. Peptide antagonists of the IL-2 receptor, including antagonists of Tac (p55) and p75 (IL-2Rβ) are also known. For example, peptide antagonists for p55 and p75 are disclosed in U.S. Pat. No. 5,635,597. These peptides are also of use in the methods disclosed herein.

In a further example, an IL-2 receptor antagonist is a chemical compound or small molecule that specifically binds to the IL-2 receptor and inhibits a biological function of the receptor.

Antibody fragment (fragment with specific antigen binding): Various fragments of antibodies have been defined, including Fab, (Fab')$_2$, Fv, and single-chain Fv (scFv). These antibody fragments are defined as follows: (1) Fab, the fragment that contains a monovalent antigen-binding fragment of an antibody molecule produced by digestion of whole antibody with the enzyme papain to yield an intact light chain and a portion of one heavy chain or equivalently by genetic engineering; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction or equivalently by genetic engineering; (4) F(Ab')$_2$, a dimer of two FAb' fragments held together by disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine in the art.

Autoimmune disorder: A disorder in which the immune system produces an immune response (e.g. a B cell or a T cell response) against an endogenous antigen, with consequent injury to tissues.

Beta interferon: Any beta interferon including interferon-beta 1a and interferon-beta 1b.

Interferon-beta 1a is a 166 amino acid glycoprotein with a predicted molecular weight of approximately 22,500 daltons. The interferon-beta 1a known as Avonex® is produced by recombinant DNA technology utilizing mammalian cells (Chinese Hamster Ovary cells) into which the human interferon-beta gene has been introduced. The amino acid sequence of Avonex® is identical to that of natural human interferon-beta. Interferon induced gene products and markers including 2', 5'-oligoadenylate synthetase, $β_2$-microglobulin, and neopterin, have been measured in the serum and cellular fractions of blood collected from patients treated with Avonex®. Avonex® was approved in 1996 and is marketed by Biogen, Inc. Avonex® has been demonstrated to decrease the number of gadolinium (Gd)-enhanced lesions in subjects who were administered the drug for two years by up to 13% and to improve approximately 22% of subjects' Expanded Disability Status Scale (EDSS) scores.

Another interferon-beta 1a was approved in 2002 and is known as Rebif®, marketed by Serono, Inc. The interferon-beta 1a known as Rebif ®, has recently been approved for treatment of relapsing-remitting MS. The primary difference between Avonex® and Rebif ® is the approved method of administration—intramuscular injection for the former and subcutaneous injection for the latter. According to Samkoff, *Hosp. Phys.*, p.21-7 (2002), Rebif® can reduce relapse rates by 33% in subjects taking the drug.

Interferon-beta 1b is a highly purified protein that has 165 amino acids and an approximate molecular weight of 18,500 daltons. An interferon-beta 1b known as Betaseron® was approved as a treatment for MS in 1993 and is marketed by Berlex Laboratories, Inc. Betaseron® is manufactured by bacterial fermentation of a strain of *Escherichia coli* that bears a genetically engineered plasmid containing the gene for human interferon-beta. The native gene was obtained from human fibroblasts and altered to substitute serine for the cysteine residue found at position 17. According to the *Physicians' Desk Reference* (1996), Betaseron® has been demonstrated to reduce the exacerbation rate in subjects taking the drug by about 31%. The mechanisms by which interferon-beta 1b exerts its actions in multiple sclerosis are not clearly understood. However, it is known that the biologic response-modifying properties of interferon-beta 1b are mediated through its interactions with specific cell receptors. The binding of interferon-beta 1b to these receptors induces the expression of a number of interferon induced gene products (e.g., 2',5'-oligoadenylate synthetase, protein kinase, and indoleamine 2,3-dioxygenase) that are believed to be the mediators of the biological actions of interferon-beta 1b.

Complementarity-determining region (CDR): The CDRs are three hypervariable regions within each of the variable light (VL) and variable heavy (VH) regions of an antibody molecule that form the antigen-binding surface that is complementary to the three-dimensional structure of the bound antigen. Proceeding from the N-terminus of a heavy or light chain, these complementarity-determining regions are denoted as "CDR1", "CDR2," and "CDR3," respectively. CDRs are involved in antigen-antibody binding, and the CDR3 comprises a unique region specific for antigen-antibody binding. An antigen-binding site, therefore, may include six CDRs, comprising the CDR regions from each of a heavy and a light chain V region. Alteration of a single amino acid within a CDR region can destroy the affinity of an antibody for a specific antigen (see Abbas et al., *Cellular and Molecular Immunology*, 4th ed. 143-5, 2000). The locations of the CDRs have been precisely defined, e.g., by Kabat et al., *Sequences of Proteins of Immunologic Interest*, U.S. Department of Health and Human Services, 1983.

Epitope: The site on an antigen recognized by an antibody as determined by the specificity of the amino acid sequence. Two antibodies are said to bind to the same epitope if each competitively inhibits (blocks) binding of the other to the antigen as measured in a competitive binding assay (see, e.g., Junghans et al., *Cancer Res.* 50:1495-1502, 1990). Alternatively, two antibodies have the same epitope if most amino acid mutations in the antigen that reduce or eliminate binding of one antibody reduce or eliminate binding of the other. Two antibodies are said to have overlapping epitopes if each partially inhibits binding of the other to the antigen, and/or if some amino acid mutations that reduce or eliminate binding of one antibody reduce or eliminate binding of the other.

Framework region (FR): Relatively conserved sequences flanking the three highly divergent complementarity-determining regions (CDRs) within the variable regions of the heavy and light chains of an antibody. Hence, the variable region of an antibody heavy or light chain consists of a FR and three CDRs. Some FR residues may contact bound antigen; however, FRs are primarily responsible for folding the variable region into the antigen-binding site, particularly the FR residues directly adjacent to the CDRs. Without being bound by theory, the framework region of an antibody serves to position and align the CDRs. The sequences of the framework regions of different light or heavy chains are relatively conserved within a species. A "human" framework region is a framework region that is substantially identical (about 85% or more, usually 90-95% or more) to the framework region of a naturally occurring human immunoglobulin.

Immunoglobulin: A protein including one or more polypeptides substantially encoded by immunoglobulin genes. The recognized immunoglobulin genes include the kappa, lambda, alpha (IgA), gamma (IgG$_1$, IgG$_2$, IgG$_3$, IgG$_4$), delta (IgD), epsilon (IgE) and mu (IgM) constant region genes, as well as the myriad immunoglobulin variable region genes. Full-length immunoglobulin light chains are generally about 25 Kd or 214 amino acids in length. Full-length immunoglobulin heavy chains are generally about 50 Kd or 446 amino acid in length. Light chains are encoded by a variable region gene at the NH2-terminus (about 110 amino acids in length) and a kappa or lambda constant region gene at the COOH—terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and (Fab')$_2$, as well as bifunctional hybrid antibodies and single chains (e.g., Lanzavecchia et al., *Eur. J. Immunol.* 17:105, 1987; Huston et al., *Proc. Natl. Acad Sci. USA.*, 85:5879-5883, 1988; Bird et al., *Science* 242:423-426, 1988; Hood et al., *Immunology, Benjamin, N.Y.*, 2nd ed., 1984; Hunkapiller and Hood, *Nature* 323:15-16, 1986).

An immunoglobulin light or heavy chain variable region includes a framework region interrupted by three hypervariable regions, also called complementarity determining regions (CDR's) (see, *Sequences of Proteins of Immunological Interest*, E. Kabat et al., U.S. Department of Health and Human Services, 1983). As noted above, the CDRs are primarily responsible for binding to an epitope of an antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody (e.g., ATCC Accession No. CRL 9688 secretes an anti-Tac chimeric antibody), although other mammalian species can be used, or the variable region can be produced by molecular techniques. Methods of making chimeric antibodies are well known in the art, e.g., see U.S. Pat. No. 5,807,715, which is herein incorporated by reference.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Exemplary conservative substitutions are those such as gly, ala; val, ile, leu; asp, glu; asn, gln; ser, thr; lys, arg; and phe, tyr (see U.S. Pat. No. 5,585,089, which is incorporated herein by reference). Humanized immunoglobulins can be constructed by means of genetic engineering, e.g., see U.S. Pat. No. 5,225,539 and U.S. Pat. No. 5,585,089, which are herein incorporated by reference.

A human antibody is an antibody wherein the light and heavy chain genes are of human origin. Human antibodies can be generated using methods known in the art. Human antibodies can be produced by immortalizing a human B cell secreting the antibody of interest. Immortalization can be accomplished, for example, by EBV infection or by fusing a human B cell with a myeloma or hybridoma cell to produce a trioma cell. Human antibodies can also be produced by phage display methods (see, e.g., Dower et al., PCT Publication No. WO91/17271; McCafferty et al., PCT Publication No. WO92/001047; and Winter, PCT Publication No. WO92/20791, which are herein incorporated by reference), or selected from a human combinatorial monoclonal antibody library (see the Morphosys website). Human antibodies can also be prepared by using transgenic animals carrying a human immunoglobulin gene (e.g., see Lonberg et al., PCT Publication No. WO93/12227; and Kucherlapati, PCT Publication No. WO91/10741, which are herein incorporated by reference).

Interleukin 2 (IL-2): A protein of 133 amino acids (15.4 kDa) with a slightly basic pI that does not display sequence homology to any other factors. Murine and human IL-2 display a homology of approximately 65%. IL-2 is synthesized as a precursor protein of 153 amino acids with the first 20 amino terminal amino acids functioning as a hydrophobic secretory signal sequence. The protein contains a single disulfide bond (positions Cys58/105) essential for biological activity. The human IL-2 gene contains four exons and maps to human chromosome 4q26-28 (murine chromosome 3).

The biological activities of IL-2 are mediated by a membrane receptor that is expressed on activated, but not on resting, T cells and natural killer (NK) cells. Activated B cells and resting mononuclear leukocytes also rarely express this receptor.

IL-2 receptor: A cellular receptor that binds IL-2 and mediates its biological effects. Three different types of IL-2 receptors are distinguished that are expressed differentially and independently. The high affinity IL-2 receptor ($K_d$~10 pM) constitutes approximately 10% of all IL-2 receptors expressed by cells. This receptor is a membrane receptor complex consisting of the two subunits: IL-2R-alpha (also known as T cell activation (TAC) antigen or p55) and IL-2R-beta (also known as p75 or CD122). An intermediate affinity IL-2 receptor ($K_d$=100 pM) consists of the p75 subunit and a gamma chain, while a low affinity receptor ($K_d$=10 nM) is formed by p55 alone.

p75 is 525 amino acids in length. It has an extracellular domain of 214 amino acids and a cytoplasmic domain of 286 amino acids. The p75 gene maps to human chromosome 22q11.2-q12, contains 10 exons and has a length of approximately 24 kb. p55 is 251 amino acids in length with an extracellular domain of 219 amino acids and a very short cytoplasmic domain of 13 amino acids. The gene encoding p55 maps to human chromosome 10p14-p15.

p75 is expressed constitutively on resting T-lymphocytes, NK cells, and a number of other cell types while the expression of p55 is usually observed only after activation. Activated lymphocytes continuously secrete a 42 kDa fragment of p55 (TAC antigen). This fragment circulates in the serum and plasma and functions as a soluble IL2 receptor (see Smith, *Ann. Rev. Cell Biol.* 5:397-425, 1989; Taniguchi and Minami, Cell 73:5-8, 1993).

p55 has a length of 251 amino acids with an extracellular domain of 219 amino acids an a very short cytoplasmic domain of 13 amino acids. The p55 gene maps to human chromosome 10p14-p15. The expression of p55 is regulated by a nuclear protein called RPT-1.

A third 64 kDa subunit of the IL2 receptor, designated gamma, has been described. This subunit is required for the generation of high and intermediate affinity IL-2 receptors but does not bind IL-2 by itself. The gene encoding the gamma subunit of the IL2 receptor maps to human chromosome Xq13, spans approximately 4.2 kb and contains eight exons.

Magnetic Resonance Imaging: A noninvasive diagnostic technique that produces computerized images of internal body tissues and is based on nuclear magnetic resonance of atoms within the body induced by the application of radio waves.

Brain MRI is an important tool for understanding the dynamic pathology of multiple sclerosis. $T_2$-weighted brain MRI defines lesions with high sensitivity in multiple sclerosis and is used as a measure of disease burden. However, such high sensitivity occurs at the expense of specificity, as $T_2$ signal changes can reflect areas of edema, demyelination, gliosis and axonal loss. Areas of gadolinium (Gd) enhancement demonstrated on $T_1$-weighted brain MRI are believed to reflect underlying blood-brain barrier disruption from active perivascular inflammation. Such areas of enhancement are transient, typically lasting <1 month. Gadolinium-enhanced $T_1$-weighted brain MRI are therefore used to assess disease activity. Most T2-weighted (T2) lesions in the central white matter of subjects with multiple sclerosis begin with a variable period of T1-weighted (T1) gadolinium (Gd) enhancement and that T1 Gd-enhancing and T2 lesions represent stages of a single pathological process. The brain MRI techniques for assessing T1 and T2 Gd-enhancing lesions are standard (e.g., see Lee et al., *Brain* 122 (Pt 7):1211-2, 1999).

Monoclonal antibody: An antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells.

Multiple sclerosis: An autoimmune disease classically described as a central nervous system white matter disorder disseminated in time and space that presents as relapsing-remitting illness in 80-85% of patients. Diagnosis can be made by brain and spinal cord magnetic resonance imaging (MRI), analysis of somatosensory evoked potentials, and analysis of cerebrospinal fluid to detect increased amounts of immunoglobulin or oligoclonal bands. MRI is a particularly sensitive diagnostic tool. MRI abnormalities indicating the presence or progression of MS include hyperintense white matter signals on T2-weighted and fluid attenuated inversion recovery images, gadolinium enhancement of active lesions, hypointensive "black holes" (representing gliosis and axonal pathology), and brain atrophy on T1-weighted studies. Serial MRI studies can be used to indicate disease progression.

Relapsing-remitting multiple sclerosis is a clinical course of MS that is characterized by clearly defined, acute attacks with full or partial recovery and no disease progression between attacks.

Secondary-progressive multiple sclerosis is a clinical course of MS that initially is relapsing-remitting, and then becomes progressive at a variable rate, possibly with an occasional relapse and minor remission.

Primary progressive multiple sclerosis presents initially in the progressive form.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "fragment" refers to a portion of a polypeptide that is at least 8, 10, 15, 20 or 25 amino acids in length. The term "functional fragments of a polypeptide" refers to all fragments of a polypeptide that retain an activity of the polypeptide (e.g., the binding of an antigen). Biologically functional fragments, for example, can vary in size from a polypeptide fragment as small as an epitope capable of binding an antibody molecule to a large polypeptide capable of participating in the characteristic induction or programming of phenotypic changes within a cell. The term "soluble" refers to a form of a polypeptide that is not inserted into a cell membrane.

Pharmaceutical agent or drug: A chemical compound or composition capable of inducing a desired therapeutic or prophylactic effect when properly administered to a subject.

Pharmaceutically acceptable carriers: The pharmaceutically acceptable carriers useful in the methods disclosed herein are conventional. *Remington's Pharmaceutical Sciences*, by E. W. Martin, Mack Publishing Co., Easton, Pa., 15th Edition (1975), describes compositions and formulations suitable for pharmaceutical delivery of the IL-2 receptor antagonists herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain non-toxic auxiliary substances, such as wetting or emulsifying agents, preservatives, salts, amino acids, and pH buffering agents and the like, for example sodium or potassium chloride or phosphate, Tween, sodium acetate or sorbitan monolaurate.

Purified: The term purified does not require absolute purity or isolation; rather, it is intended as a relative term. Thus, for example, a purified or isolated protein preparation is one in which protein is more enriched than the protein is in its generative environment, for instance within a cell or in a biochemical reaction chamber. Preferably, a preparation of protein is purified such that the protein represents at least 50% of the total protein content of the preparation. For pharmaceuticals, "substantial" purity of 90%, 95%, 98% or even 99% or higher of the active agent can be utilized.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of the IL-2R antibodies or antigen binding fragments, and the corresponding cDNA sequence, will possess a relatively high degree of sequence identity when aligned using standard methods. This homology will be more significant when the orthologous proteins or cDNAs are derived from species that are more closely related, compared to species more distantly related (e.g., human and murine sequences).

Methods of alignment of sequences for comparison are well known in the art. Various programs and alignment algorithms are described in Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244 9, 1988); Higgins and Sharp, *CABIOS* 5:151-153, 1989; Corpet et al., *Nuc. Acids Res.* 16:10881-90, 1988; Huang et al., *Computer Appls. in the Biosciences* 8:155-65, 1992; and Pearson et al., *Meth. Mol. Bio.* 24:307-31, 1994. Altschul et al., *J. Mol. Biol.* 215:403-410, 1990, presents a detailed consideration of sequence alignment methods and homology calculations.

Specific binding agent: An agent that binds substantially only to a defined target. Thus an IL-2 receptor-specific binding agent binds substantially only the IL-2 receptor, or a component thereof. As used herein, the term "IL-2 receptor-specific binding agent" includes anti-IL-2 receptor antibodies and other agents that bind substantially only to an IL-2 receptor or a component thereof (e.g., p55, p75).

Anti-IL-2 receptor antibodies may be produced using standard procedures described in a number of texts, including Harlow and Lane (*Using Antibodies, A Laboratory Manual*, CSHL, New York, 1999, ISBN 0-87969-544-7). In addition, certain techniques may enhance the production of neutralizing antibodies (U.S. Pat. No. 5,843,454; U.S. Pat. No. 5,695,927; U.S. Pat. No. 5,643,756; and U.S. Pat. No. 5,013,548). The determination that a particular agent binds substantially only to an IL-2 receptor component may readily be made by using or adapting routine procedures. One suitable in vitro assay makes use of the Western blotting procedure (described in many standard texts, including Harlow and Lane, 1999). Western blotting may be used to determine that a given protein binding agent, such as an anti-IL-2 receptor monoclonal antibody, binds substantially only to the IL-2 receptor. Antibodies to the IL-2 receptor are well known in the art.

Shorter fragments of antibodies can also serve as specific binding agents. For instance, Fabs, Fvs, and single-chain Fvs (SCFvs) that bind to an IL-2 receptor would be IL-2 receptor-specific binding agents.

Subject: A human or non-human animal. In one embodiment, the subject has multiple sclerosis.

A subject who has multiple sclerosis who has failed a therapeutic protocol (such as administration of interferon-beta) is a subject who does not respond or fails to respond adequately to the therapy, such that their condition has not improved sufficiently, not changed, or deteriorated in response to treatment with a therapeutically effective amount of the drug. A subject who has failed a therapeutic protocol can require escalating doses of the drug to achieve a desired effect.

In one example, the failure of a subject with MS to respond to a therapeutic agent, such as interferon-beta, can be measured as a recurrence of Gd-contrasting MRI lesions to at least half of the mean of the baseline monthly contrasting lesions over six months. In other examples, a subject with MS that fails to respond to a therapeutic agent, such as interferon-beta treatment, is identified by the subject experiencing one or more exacerbations in an 18 month period of interferon-beta therapy, exhibiting an increase of 1 point or more on the EDSS over 18 months of treatment, or having persistence or reoccurrence of contrast enhancing lesions on brain MRI scans to at least one-half the mean of a baseline of monthly contrast enhancing lesions established over a 6-month baseline period measured prior to the beginning of the interferon-beta therapy.

Without being bound by theory, a subject can fail to respond to IFN treatment due to the development of neutralizing antibodies, although a failure to respond to IFN treatment can also be detected in the absence of neutralizing antibodies (primary failure). In one example, a subject who fails treatment with interferon-beta is a subject who develops neutralizing antibodies that specifically bind interferon-beta, such that escalating doses are required to see an effect, or to alter a sign or symptom of MS.

Symptom and sign: Any subjective evidence of disease or of a subject's condition, i.e., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for immunological status or the presence of lesions in a subject with multiple sclerosis.

Therapeutically Effective Amount: A dose sufficient to prevent advancement, or to cause regression of the disease, or which is capable of reducing symptoms caused by the disease, such as multiple sclerosis.

Zenapax® (daclizumab): A particular recombinant, humanized monoclonal antibody of the human IgG1 isotype that specifically binds Tac (p55). The recombinant genes encoding Zenapax® are a composite of human (about 90%) and murine (about 10%) antibody sequences. The donor murine anti-Tac antibody is an IgG2a monoclonal antibody that specifically binds the IL-2R Tac protein and inhibits IL-2-mediated biologic responses of lymphoid cells. The murine anti-Tac antibody was "humanized" by combining the complementarity-determining regions and other selected residues of the murine anti-TAC antibody with the framework and constant regions of the human IgG1 antibody. The humanized anti-Tac antibody daclizumab is described and its sequence is set forth in U.S. Pat. No. 5,530,101, see SEQ ID NO: 5 and SEQ ID NO: 7 for the heavy and light chain variable regions respectively. U.S. Pat. No. 5,530,101 and Queen et al., *Proc. Natl. Acad. Sci.* 86:1029-1033, 1989 are both incorporated by reference herein in their entirety. Daclizumab inhibits IL-2-dependent antigen-induced T cell proliferation and the mixed lymphocyte response (MLR) (Junghans et al., *Cancer Research* 50:1495-1502, 1990), as can other antibodies of use in the methods disclosed herein.

Zenapax® has been approved by the U.S. Food and Drug Administration (FDA) for the prophylaxis of acute organ rejection in subjects receiving renal transplants, as part of an immunosuppressive regimen that includes cyclosporine and coritcosteroids. Zenapax® has been shown to be active in the treatment of human T cell lymphotrophic virus type 1 associated myelopathy/topical spastic paraparesis (HAM/TSP, see Lehky et al., *Ann. Neuro.,* 44:942-947, 1998). The use of Zenapax® to treat posterior uveitis has also been described (see Nussenblatt et al., *Proc. Natl. Acad. Sci.,* 96:7462-7466, 1999).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety for all purposes. In case of conflict, the present specification, including explanations of terms, will control. In addition, the materials, methods, and examples are illustrative only and not intended to be limiting.

Methods for Treating Subject with Multiple Sclerosis

Methods are provided herein for the treatment of subjects that have multiple sclerosis. In one embodiment the subject has relapsing-remitting multiple sclerosis. However, the methods disclosed herein can also be used for the treatment of subjects with other forms of mulitiple sclerosis, such as secondary or primary progressive multiple sclerosis.

In certain embodiments the method is used to treat subjects who have failed to respond adequately to interferon-beta treatment alone. A failure to respond to interferon-beta treatment alone is, in some examples, demonstrated by the subject experiencing one or more exacerbations in an 18 month period of interferon-beta therapy, an increase of 1 point or more on the EDSS over 18 months of treatment, or persistence or reoccurrence of contrast enhancing lesions on brain MRI scans to at least one-half the mean of a baseline of monthly contrast enhancing lesions established over a 6-month baseline period measured prior to the beginning of the interferon-beta therapy. Other indicators of disease progression or activity known to those with skill in the art can also be used to determine whether a subject has failed to respond to interferon-beta therapy. The interferon-beta therapy can be treatment with interferon-beta 1b, interferon-beta 1a, or both types of interferon.

In a specific embodiment, a therapeutically effective amount of an IL-2 receptor (IL-2R) antagonist is administered to the subject without the concurrent administration of interferon-beta. A single IL-2R antagonist can be utilized, or a combination of IL-2R antagonists can be utilized in the treatment of multiple sclerosis. The IL-2R antagonist is any agent that binds to the IL-2R on activated T-lymphocytes and inhibits the activity of the receptor.

In one specific non-limiting example, the IL-2 receptor antagonist is an antibody, such as a monoclonal antibody, e.g., a chimeric, humanized or human monoclonal antibody. A specific example of a humanized monoclonal antibody that specifically binds p55 is daclizumab, which is described and its sequence is set forth in U.S. Pat. No. 5,530,101, which is incorporated by reference herein, and in Queen et al., *Proc. Natl. Acad. Sci.* 86:1029-1033, 1989. Thus, the antibody can be a humanized immunoglobulin having complementarity determining regions (CDRs) from a donor immunoglobulin and heavy and light chain variable region frameworks from human acceptor immunoglobulin heavy and light chain frameworks, wherein the humanized immunoglobulin specifically binds to a human interleukin-2 receptor with an affinity constant of at least $10^8$ $M^{-1}$. The sequence of the humanized immunoglobulin heavy chain variable region framework can be at least 65% identical to the sequence of the donor immunoglobulin heavy chain variable region framework. A specific example of the variable region of the anti-Tac antibody is set forth as SEQ ID NO: 1 and SEQ ID NO: 3 of U.S. Pat. No. 5,520,101 (light and heavy chain, respectively), and the variable region of the humanized anti-Tac antibody daclizumab is set forth as SEQ ID NO: 5 and SEQ ID NO: 7 (heavy and light chain, respectively) of U.S. Pat. No. 5,530,101, which is herein incorporated by reference.

The antibody can include two light chain/heavy chain dimers, and specifically binds to either p55 (such as the anti-Tac antibody) or p75. Il-2R antagonists of use include agents that bind specifically to p55 (also known as the alpha chain or Tac subunit) of the human IL-2R. In one example, the agent is a monoclonal antibody, such as daclizumab, basiliximab, BT563, and 7G8 or their chimeric or humanized forms. The agent can also be a human antibody, or a humanized antibody with synthetic CDRs that specifically binds p55. Antibodies that bind the same (or overlapping) epitope as daclizumab or basiliximab can also be used in the methods disclosed herein. In other embodiments, the antibody will have high sequence identity with daclizumab or basiliximab, at least 90 or 95%, such as at least 98% or 99% sequence identity, while retaining the functional properties of the antibody, i.e., its antagonist properties to the IL-2R. The antibody may be of any isotype, but in several embodiment that antibody is an IgG, including but not limited to, IgG1, IgG2, IgG3 and IgG4.

In other embodiments the antibody is basilimab, marketed as Simulect® by Novartis Pharma AG. Simulect® is a chimeric (murine/human) monoclonal antibody (IgG$_1$κ), produced by recombinant DNA technology, that functions as an immunosuppressive agent, specifically binding to and blocking the alpha chain of the IL-2R on the surface of activated T-lymphocytes. Simulect® is a glycoprotein obtained from fermentation of an established mouse myeloma cell line genetically engineered to express plasmids containing the human heavy and light chain constant region genes and mouse heavy and light chain variable region genes encoding the RFT5 antibody that binds selectively to the IL-2R(alpha). Based on the amino acid sequence, the calculated molecular weight of the protein is 144 kilodaltons.

Alternatively, the IL-2R antagonist is a molecule that binds to other subunits of the IL-2 receptor, such as Mik-β1 or Mik-β2 or their chimeric or humanized versions, which bind to the beta chain of human IL-2R, or another antibody that specifically binds p75 (see U.S. Pat. No. 5,530,101, which is incorporated herein by reference). The IL-2R antagonist may also be a fragment of an antibody (e.g., a chimeric, humanized, or human antibody) such as an Fab, (Fab')$_2$, Fv, or scFv. Further, the fragment may be pegylated to increase its half-life.

In some examples, the IL-2R antagonist is a combination of anti-IL-2R agents. For example, Zenapax® and Simulect® are administered together as a cocktail, or the agents are alternated in the administration schedule.

The IL-2R antagonist, such as a humanized antibody that specifically binds the IL-2R, can be used in combination with other antibodies, particularly human monoclonal antibodies reactive with other markers on cells responsible for a disease. For example, suitable T cell markers can include those grouped into the so-called "Clusters of Differentiation," (CD antigens, see the First International Leukocyte Differentiation Workshop, Leukocyte Typing, Bernard, et al., Eds., Springer-Verlag, N.Y., 1984). In another example, the other antibody binds and inhibits a lymphokine, such as IFN-gamma, or a lymphokine receptor. In one example, the other antibody binds α5β1 integrin (VLA-5), of which a particularly preferred exemplary antibody is Antegren® (Elan Pharmaceuticals and Biogen, Inc.).

The IL-2R antagonist can be administered parenterally, i.e., subcutaneously, intramuscularly or intravenously or by means of a needle-free injection device. The compositions for parenteral administration will commonly include a solution of the IL-2R antagonist (e.g. the antibody) in a pharmaceutically acceptable carrier as described above. The concentration of antibody in the formulations can vary widely, i.e., from less than about 0.5%, usually at or at least about 1% to as much as 15 or 20% by weight or from 1 mg/mL to 100 mg/mL. The concentration is selected primarily based on fluid volumes, viscosities, etc., in accordance with the particular mode of administration selected.

Methods for preparing pharmaceutical compositions are known those skilled in the art (see Remington's Pharmaceutical Science, 15th ed., Mack Publishing Company, Easton, Pa., 1980).

Antibodies of use in the methods disclosed herein can be frozen or lyophilized for storage and reconstituted in a suitable carrier prior to use. One of skill in the art can readily design appropriate lyophilization and reconstitution techniques.

The IL-2R antagonist can be administered for therapeutic treatments of a subject with multiple sclerosis. Thus, a therapeutically effective amount of a composition is administered to a subject already suffering from MS, in an amount sufficient to improve a sign or a symptom of the disorder. Generally a suitable dose of Zenapax® (daclizumab) is about 0.5 milligram per kilogram (mg/kg) to about 3 mg/kg, such as a dose of about 1 mg/kg, about 1.5 mg/kg, about 2 mg/kg, or about 2.5 mg/kg administered intraveneously or subcutaneously. Unit dosage forms are also possible, for example 50 mg, 100 mg, 150 mg or 200 mg, or up to 400 mg per dose. However, other higher or lower dosages also could be used, such as from about 0.5 to about 8 mg/kg. It has been suggested that that serum levels of 5 to 10 µg/mL are necessary for saturation of the Tac subunit of the IL-2 receptors to block the responses of activated T lymphocytes. One of skill in the art will be able to construct an administration regimen to keep serum levels within that range, although administration resulting in higher or lower serum levels could be used. Doses of Simulect® are likely to be lower, for example 0.25 mg/kg to 1 mg/kg, e.g., 0.5 mg/kg, or unit doses of 10, 20, 40, 50 or 100 mg. The general principle of keeping the IL-2R saturated could also be used to guide the choice of dose levels of other IL-2R antagonists such as other monoclonal antibodies.

Single or multiple administrations of the IL-2R antagonist compositions can be carried out with dose levels and pattern being selected by the treating physician. Generally, multiple doses are administered. In several examples, multiple administrations of Zenapax® (daclizumab) or other IL-2R antibodies are utilized, such as administration monthly, bimonthly, every 6 weeks, every other week, weekly or twice per week. An exemplary protocol for administration of Zenapax® (daclizumab), also applicable to other IL-2R antibodies, is described in the examples section below. For an IL-2R antagonist that is not an antibody, more frequent administration may be necessary, for example, one, two, three of four or more times per day, or twice per week. Such an IL-2R antagonist can be administered orally, but subcutaneous or intravenous administration can also be utilized. Treatment will typically continue for at least a month, more often for two or three months, sometimes for six months or a year, and may even continue indefinitely, i.e., chronically. Repeat courses of treatment are also possible.

In one embodiment, the IL-2R antagonist is administered without concurrent administration of an interferon-beta, such as interferon-beta-1a or interferon-beta-1b. In one specific, non-limiting example, Zenapax® (daclizumab) is administered without concurrent administration of an interferon-beta, such as interferon-beta-1a or interferon-beta-1b. In another specific, non-limiting example, Zenapax® (daclizumab) is administered without concurrent administration of other additional pharmaceutical agents to treat multiple sclerosis, such as other immunosuppressive agents.

In another embodiment, a therapeutically effective amount of an IL-2 receptor antagonist is administered in combination with an interferon-beta, such as interferon-beta-1a or interferon-beta-1b.

If the interferon-beta is interferon-beta 1b (e.g., Betaseron®), an exemplary dose is 0.25 mg by subcutaneous injection every other day. However, higher or lower doses can be used, for example from 0.006 mg to 2 mg daily, biweekly, weekly, bimonthly or monthly. If the interferon-beta is interferon-beta 1a and is Avonex®, an exemplary dose is 30 μg injected intramuscularly once a week. However, higher or lower doses could be used, for example 15 to 75 μg daily, biweekly, weekly, bimonthly or monthly. If the interferon-beta 1a is Rebif®, an exemplary dose is 44 μg three times per week by subcutaneous injection. However, higher or lower doses can be used, including treatment daily, biweekly, weekly, bimonthly, or monthly. Additionally, the dosage may be changed during the course of therapy. For example, Rebif® can be administered at an initial dose of 8.8 μg for the first two weeks, then 22 μg for the next two weeks, and then at 44 μg for the rest of the therapy period. In specific embodiments, Avonex® can be administered at a dose of 30 μg per week or Betaseron® can be administered at a dose of 0.25 mg every other day.

Administration of interferon-beta also can be performed on strict or adjustable schedules. For example, interferon-beta is administered once weekly, every-other-day, or on an adjustable schedule, for example based on concentration in a subject. One of skill in that art will realize that the particular administration schedule will depend on the subject and the dosage being used. The administration schedule can also be different for individual subjects or change during the course of the therapy depending on the subject's reaction. In specific examples, interferon-beta 1a is administered every other week, or monthly.

The combined administration of the IL-2R antagonist and interferon-beta includes administering interferon-beta either sequentially with the IL-2R antagonist, i.e., the treatment with one agent first and then the second agent, or administering both agents at substantially the same time, i.e., an overlap in performing the administration. With sequential administration a subject is exposed to the agents at different times so long as some amount of the first agent remains in the subject (or has a therapeutic effect) when the other agent is administered. The treatment with both agents at the same time can be in the same dose, i.e., physically mixed, or in separate doses administered at the same time.

In a particular embodiment interferon-beta 1a (e.g., Avonex®) is administered weekly via intramuscular injection. The first week of therapy the subject receives an intravenous infusion of the monoclonal antibody (e.g., Zenapax®) at the same time as the interferon-beta 1a injection, with a second humanized anti-Tac monoclonal antibody (e.g., Zenapax®) infusion being administered two weeks later at the same time as the interferon-beta 1a (e.g. Avonex®) injection. Thereafter the humanized anti-Tac monoclonal antibody (e.g., Zenapax®) is administered monthly at the same time as the weekly interferon-beta 1a injection. In another embodiment interferon-beta 1b (e.g. Betaseron®) is administered every other day via subcutaneous injection while the humanized anti-Tac monoclonal antibody (e.g., Zenapax®) is administered every other week for one month, and then monthly, with the humanized anti-Tac monoclonal antibody (e.g., Zenapax®) infusion not necessarily on the same day as the interferon-beta 1b (e.g., Betaseron®) injection.

The IL-2R antagonist may also be used in combination with one or more other drugs that may be active in treating multiple sclerosis. These include, but are not limited to, Copaxone®, corticosteroids such as prednisone or methylprednisolone; immunosuppressive agents such as cyclosporine (or other calcineurin inhibitors, such as Prograf®), azathioprine, Rapamune® and Cellcept®; anti-metabolites such as methotrexate; and antineoplastic agents such as mitoxantrone.

Treatment with the IL-2R antagonist, alone or in combination with other agents, will on average reduce the number of gadolinium enhanced MRI lesions by at least 30%. In one embodiment, the gadolinium enhanced MRI lesions are reduced by at least about 50% or by at least about 70%, such as a reduction of about 80%, about 90%, or by more than 95%, as compared to baseline measurements for the same subjects or to measurement in control subjects (e.g. subjects not receiving the IL-2R antagonist). Similarly, treatment with the IL-2R antagonist, alone or in combination with other agents, will reduce the average number of MS exacerbations per subject in a given period (e.g., 6, 12, 18 or 24 months) by at least about 25%, such as at least about 40% or at least about 50%. In one embodiment, the number of MS exacerbations is reduced by at least about 80%, such as at least about 90%, as compared to control subjects. The control subjects can be untreated subject or subjects not receiving the IL-2R antagonist (e.g., subjects receiving other agents). Treatment with the IL-2R antagonist, alone or in combination with other agents, can also reduce the average rate of increase in the subject's disability score over some period (e.g., 6, 12, 18 or 24 months), e.g., as measured by the EDSS score, by at least about 10% or about 20%, such as by at least about 30%, 40% or 50%. In one embodiment, the reduction in the average rate of increase in the ESS score is at least about 60%, at least about 75%, or at least about 90%, or can even lead to actual improvement in the disability score, compared to control subjects, such as untreated subjects or subjects not receiving the IL-2R antagonist but possibly receiving other agents. These benefits can be demonstrated in one or more randomized, placebo-controlled, double-blinded, Phase II or III clinical trials and will be statistically significant (e.g., $p<0.05$).

The present disclosure is illustrated by the following non-limiting Examples.

EXAMPLES

Example 1

Protocol for the Use of a Humanized IL-2R Antibody (Zenapax®) to Treat Multiple Sclerosis A. Objectives A study was conducted to determine the efficacy of Zenapax® therapy in subjects with multiple sclerosis who have failed standard IFN-β therapy by comparing the mean number of Gd-enhancing lesions during the pre-treatment period to that of the treatment period. This study was also demonstrated the safety and tolerability of Zenapax® in subjects with multiple sclerosis using clinical, MRI, and immunologic measures.

In order to assess the efficacy of Zenapax® therapy in subjects with multiple sclerosis who had failed standard IFN-β therapy the following measures were used:
1. MRI measures
   T2 lesion load,
   Volume of Gd-enhancing lesions,
   Volume of T1 hypointensities (optional);
2. Clinical measures, specifically,
   Change in EDSS, change in SRS (Scripps Neurological Rating Scale)
   Relapse rate; 9-hole peg test
3. Immunologic measures, specifically,
   Markers of Th1 and Th2 T cell lineages, as well as FACS analysis of
   various T cell markers,
   Cytokine production by T cells in vitro,
   Proliferation of T cells For purposes of the study, failure to respond to standard IFN-β therapy was defined as a recurrence of Gd-contrasting MRI lesions to at least half the mean of baseline monthly Gd-contrasting lesions over 6 months before onset of IFN treatment or primary non-responsiveness to IFN treatment or the presence of clinical relapses during the last 12 months. The subjects tested were primary IFN-β non-responders, i.e., in the absence of neutralizing antibodies against IFN-β, or secondary non-responders, i.e., in the presence of neutralizing antibodies.

B. Study Outline

Subjects were enrolled following completion of all pre-screening (Week -8) procedures provided that failure to standard IFN-β therapy was documented. After enrollment, subjects underwent three Gd-enhanced MRIs at 4-week intervals prior to the first dose of study drug. Subjects with at least 2 Gd-enhancing lesions or greater in the 3 pre-treatment MRI scans (an average of at least 0.67 Gd-enhancing lesions per scan) were eligible to proceed to the treatment phase of the study. During the treatment phase, subjects received seven IV infusions of 1 mg/kg body weight anti-interleukin-2 receptor alpha subunit (IL-2Rα; Zenapax®), day 0, week 2, week 6, week 10, week 14, week 18 and week 22; total of 7 doses) for 5.5 months=22 weeks, and continued to undergo Gd-enhanced MRIs at 4-week intervals. Following the last dose of study drug, subjects were monitored for 12 weeks. Some subjects continued to receive standard IFN-β therapy throughout the trial, while IFN-β therapy was discontinued in some subjects.

B.1 Inclusion and Exclusion Criteria for Pre-Treatment Screening

Candidates for the study met the following criteria at the time of enrollment (Table 1):

TABLE 1

Inclusion Criteria

1) Between the ages of 18 and 65 years, inclusive.
2) Subjects with relapsing-remitting or secondary progressive MS who had more than one relapse within 18 months preceding study enrollment. Subjects had at least 2 Gd-enhancing lesions or greater in the 3 pre-treatment MRI scans (an average of at least 0.67 Gd-enhancing lesions per scan).
3) EDSS score between 1–6.5, inclusive.
   Subjets who have failed standard IFN-β therapy. IFN-β treatment failures were specified as follows: Individuals who had received IFN TABLE 1-continued Inclusion Criteria treatment for at least 6–12 months and had more than one exacerbation during the past year which required treatment by intravenous steroids. Subjects currently enrolled in a protocol for the administration of both Zenapax ® and IFN-β were eligible for rollover into either a dose escalation phase or the Zenapax ® single therapy phase after 5.5 months of therapy. Those subjects that had a 75% or greater decrease in lesion activity were eligible for the Zenapax ® single dose phase, while those subjects that failed to achieve at least a 75% reduction in lesion activity were eligible for the dose escalation phase.

Candidates were excluded from study entry if any of the exclusion criteria existed at the time of enrollment (Table 2):

TABLE 2

Exclusion Criteria

Medical History

1) Diagnosis of primary progressive MS, defined as gradual progression of disability from the onset without relapses.
2) Abnormal screening/pre-treatment blood tests exceeding any of the limits defined below:
   Alanine transaminase (ALT) or aspartate transaminase (AST) > two times the upper limit of normal (i.e., >2 × ULN)
   Total white blood cell count <3,000/mm$^3$
   CD4$^+$ count <320/mm$^3$
   Platelet count <80,000/mm$^3$
   Creatinine >2.0 mg/dL
3) Concurrent, clinically significant (as determined by the investigator) cardiac, immunologic, pulmonary, neurologic, renal, and/or other major disease.
4) Any contraindication to monoclonal antibody therapies.
5) Subjects who were HIV+.

Treatment History

5) If prior treatment was received, the subject were off treatment for the required period prior to enrollment (see insert).

Restrictions on Treatments

| Agent | Time Required off Agent Prior to Enrollment |
|---|---|
| Glatiramer acetate (Copaxone ®), cyclophosphamide (Cytoxan ®) | 26 weeks |
| IV Ig, azathioprine (Imuran ®), methotrexate, plasma exchange, cyclosporine, oral myelin, cladribine, mitoxantrone | 12 weeks |
| Corticosteroids, ACTH | 8 weeks |

6) Prior treatment with any other investigational drug or procedure for MS.
7) History of alcohol or drug abuse within the 5 years prior to enrollment.
8) Male and female subjects not practicing adequate contraception.
9) Female subjects who are not post-menopausal or surgically sterile who are not using an acceptable method of contraception. Acceptability of various methods of contraception will be at the discretion of the investigator. Written documentation that the subject is post-menopausal or surgically sterile must be available prior to study start.
10) Unwillingness or inability to comply with the requirements of this protocol including the presence of any condition (physical, mental, or social) that is likely to affect the subject's returning for follow-up visits on schedule.
11) Previous participation in this study.
12) Breastfeeding subjects.

A cohort of subjects entered the protocol described that failed to show at least a 75% reduction in lesion frequency on interferon and Zenapax® had the dose of Zenapax® increased to 2 mg/kg in order to assess whether this dose of Zenapax® is safe and well tolerated.

B.2 Treatment Agent and Infusion

Subjects enrolled in the study were given Zenapax® at designated time points. The anti-Tac formulation contains 5 mg/ml Zenapax® and 0.2 mg/ml Polysorbate-80 in 67 mM phosphate buffer, pH adjusted to 6.9. The formulation was packaged in a 5 ml volume of appropriate size in flint glass vials. The agent was stored at 2-8° C. away from light. The appropriate quantity of antibody solution at 5 mg/ml was diluted with 50 ml of normal saline in a mini-bag. The diluted antibody was stored for 24 hours at 2-8° C. before administration. Therapy was administered intravenously at a dose of 1 mg of Zenapax® per kg, as a 15 minute intravenous infusion. At the end of the infusion, the line was flushed with 10 ml saline. The time of administrations and vial signs were recorded on the infusion sheet. Vital signs were taken and recorded pre-infusion, immediately post infusion, and 15 minutes after the infusion is completed. The maximum dose of the study drug was 20 ml, which is the equivalent to 200 mg of antibody.

The vials of Zenapax® were vented prior to withdrawing the contents. A venting needle, or a 20-22G needle attached to a syringe (without the plunger) was, in some cases, be inserted into the vials. Air was not injected into the headspace of the vials or into the solution. After ventilation, the contents were withdrawn from each of the vials into a syringe (with a 20-22 G needle) large enough to hold the total calculated dose of Zenapax®.

A syringe and needle was used to remove a volume of saline equivalent to the calculated dose of Zenapax® (plus any overfill) from a 150 ml container of sterile water, although alternatively normal saline (0.9% NaCl USP) can be used. The contents of the syringe holding the Zenapax® was injected into the container. The contents were mixed by gently rocking the container for about 20 seconds, such that the reconstituted product was ready for infusion. The diluted Zenapax® solution was stored at room temperature. The diluted solution was completely infused within 4 hours after dilution.

Standard clinical practice for ensuring sterility of the infusion material was followed. Zenapax® was administered by a dedicated intravenous line at a constant rate over 15 minutes and was followed by a normal saline flush. To control the rate, an infusion pump was used. Volume of the saline flush was no less than the residual volume of the solution retained in the IV tubing. New tubing was used for each infusion.

Subjects were required to receive their infusion within 7 days of scheduled appointments. Subjects were examined at each study visit prior to initiation of the infusion. All subjects used accepted birth control methods for six months after completion of treatment, and female subjects were not pregnant.

Zenapax® was administered as a 15-minute IV infusion of 1 mg/kg (based on ideal body weight) at day 0, week 2, week 6, week 10, week 14, week 18 and week 22; total of 7 doses) for 5.5 months=22 weeks after all other required procedures at each visit was performed. MRIs occurred within 7 days prior to study drug dosing. In a few subjects, two additional infusions at 6 weeks intervals were given at weeks 28 and 34.

C. Treatment Schedule, Including Tests and Evaluations

The sample size for the initial study disclosed herein, 10 treated subjects, was chosen according to extensive experience during MS natural history studies, an IFN-β1b MRI study and statistical evaluation of these data.

Tests were performed according to the schedule shown in Table 3.

TABLE 3

Test and Evaluation Schedule

1. Week-8 (Screening Visit)
   Unless otherwise specified, the tests and evaluations were performed within 7 days prior to the subject's first MRI to determine subject eligibility:
   A complete medical history.
   Vaccination status.
   A complete physical examination including measurement of vital signs and body weight.
   Chest x-ray.
   ECG.
   Blood chemistries.
   Hematology: CBC with differential and platelet count.
   $CD4^+$ count.
   Immunologic measures.
   Urine pregnancy test for women of child-bearing potential.
   Testing for antibodies to Zenapax ® (serum stored until analysis).
   EDSS/SRS/9-hole peg test.
   MRI (performed after all other screening procedures were completed).
   Skin test with multiple recall antigens; alternatively performed at week-4
   Serum for determination anti-IL-2Rα serum levels (stored until analysis)
   HIV-I status
2. Week-4
   Vital signs.
   Immunologic measures.
   Urine pregnancy test for women of child-bearing potential.
   EDSS/SRS/9-hole peg test.
   MRI.
   Rubeola titer, EBNA titer (standard).
3. Between Weeks-4 and 0
   Optional lumbar puncture.
   Lymphacytopheresis.
4. Week 0
   Vital signs.
   Total lymphocyte count (results were available prior to dosing).
   Blood chemistries.
   Hematology: CBC with differential and platelet count.
   $CD4^+$ count.
   Urine pregnancy test for women of child-bearing potential.
   EDSS/SRS/9-hole peg test.
   MRI.
   Immunologic measures.
   Testing for antibodies to Zenapax ® (serum stored until analysis).
   Serum for determination anti-IL-2Rα serum levels (stored until analysis).
   Subject received first dose of study drug.
5. Week 2
   Vital signs.
   Total lymphocyte count (results were available prior to dosing).
   Blood chemistries.
   Hematology: CBC with differential and platelet count.
   $CD4^+$ count.
   Immunologic measures.
   Urine pregnancy test for women of child-bearing potential.
   EDSS/SRS/9-hole peg test.
   MRI.
   Infusion of Zenapax ®
   Testing for antibodies to Zenapax ® (serum stored until analysis).
   Serum for determination anti-IL-2Rα serum levels (stored until analysis)
6. Week 4
   Vital signs
   EDSS
   MRI
   Testing for antibodies to Zenapax ® (serum stored until analysis).
   Serum for determination anti-IL-2Rα serum levels (stored until analysis)
7. Week 6
   Vital signs.
   Total lymphocyte count (results were available prior to dosing).
   Blood chemistries.
   Hematology: CBC with differential and platelet count.

TABLE 3-continued

Test and Evaluation Schedule

CD4+ count.
Immunologic measures.
Urine pregnancy test for women of child-bearing potential.
EDSS/SRS/9-hole peg test.
MRI.
Infusion of Zenapax ®.
Testing for antibodies to Zenapax ® (serum stored until analysis).
Serum for determination anti-IL-2Rα serum levels (stored until analysis)
8. Week 10
Vital signs.
Total lymphocyte count (results were available prior to dosing).
Blood chemistries.
Hematology: CBC with differential and platelet count.
CD4+ count.
Immunologic measures.
Urine pregnancy test for women of child-bearing potential.
Testing for antibodies to Zenapax ®
EDSS/SRS/9-hole peg test.
MRI.
Infusion of Zenapax ®.
Testing for antibodies to Zenapax ® (serum will be stored until analysis).
Serum for determination anti-IL-2Rα serum levels (stored until analysis)
9. Week 14
Vital signs.
Total lymphocyte count (drawn so that results were available prior to dosing).
Blood chemistries.
Hematology: CBC with differential and platelet count.
CD4+ count.
Immunologic measures.
Urine pregnancy test for women of child-bearing potential.
EDSS/SRS/9-hole peg test.
MRI.
Infusion of Zenapax ®.
Testing for antibodies to Zenapax ® (serum stored until analysis).
Serum for determination anti-IL-2Rα serum levels (stored until analysis)
10. Week 18
Vital signs.
Total lymphocyte count (results were available prior to dosing).
Blood chemistries.
Hematology: CBC with differential and platelet count.
CD4+ count.
Immunologic measures.
Urine pregnancy test for women of child-bearing potential.
EDSS/SRS/9-hole peg test.
MRI.
Infusion of Zenapax ®.
Testing for antibodies to Zenapax ® (serum stored until analysis).
Serum for determination anti-IL-2Rα serum levels (stored until analysis)
11. Week 22
Vital signs.
Total lymphocyte count (results were available prior to dosing).
Blood chemistries.
Hematology: CBC with differential and platelet count.
CD4+ count.
Immunologic measures.
Urine pregnancy test for women of child-bearing potential.
EDSS/SRS/9-hole peg test.
MRI.
Infusion of Zenapax ®.
Skin test with multiple antigens (see Appendix I)
Testing for antibodies to Zenapax ® (serum stored until analysis).
Serum for determination anti-IL-2Rα serum levels (stored until analysis)
12. Week 26
Vital signs.
Blood chemistries.
Hematology: CBC with differential and platelet count.
CD4+ count.
Urine pregnancy test for women of child-bearing potential.
EDSS/SRS/9-hole peg test.
MRI.

TABLE 3-continued

Test and Evaluation Schedule

Immunologic measures.
Testing for antibodies to Zenapax ® (serum stored until analysis).
Serum for determination anti-IL-2Rα serum levels (stored until analysis)
Optional lumbar puncture.
Lymphocytopheresis.
13. Between Weeks 30 and 34
Immunologic Measures
Others (Chest X-ray, EKG)
EDSS/SRS/9-hole peg test.
MRI
Rubeola titer/EBNA titer (standard).
Testing for antibodies to Zenapax ® (serum stored until analysis).
Serum for determination anti-IL-2Rα serum levels (stored until analysis)

As indicated above, a few subjects received two more Zenapax® infusions at weeks 28 and 34 and then the same post-treatment follow-up (see Table 3, #12 and #13).

Example 2

Outcome Measures: Data Analysis

In addition to the tests and evaluations listed in Table 3, the following clinical efficacy assessments were performed during the study:
1. EDSS/SRS/9-hole peg test—measures of disability
2. Number of relapses. Relapses are defined as new or recurrent neurologic symptoms, not associated with fever or infection, lasting for at least 48 hours and accompanied by objective neurological findings upon examination.

Clinical safety was assessed by neurologic status, general physical examination, measurement of vital signs (temperature, heart rate, and blood pressure). Adverse events were collected throughout the study.

The following laboratory efficacy assessments were also performed during the study:
1. Brain MRI with and without gadolinium enhancement; additional MRI parameters
2. Immunologic measures.

The specific laboratory parameters evaluated in this study were as follows:
1. MRI activity as monitored by the physicians
2. Blood chemistry: creatinine, total bilirubin, ALT, AST, alkaline phosphatase, and albumin. Rubella- and Anti EBV-EBNA antibodies.
3. Hematology: complete blood count with differential and platelet count.

The safety assessments were as follows:
1. Analysis of peripheral CD4+ subsets was performed using flow cytometry with well-defined subset markers for T lymphocytes.
2. Collection of 4 mL whole blood (to obtain 2 mL of serum) for determination of antibody formation to Zenapax®.
3. Safety in terms of influence of Zenapax® on CNS inflammatory disease activity was documented and followed by MRI. An unexpected and potentially alerting increase in MRI activity was defined as a greater than 3-fold increase in subjects with mean pre-treatment Gd-lesion loads of <10 lesions/month. In subjects with mean pre-treatment Gd-lesion loads <3 lesions/ month, a >ten-fold increase raised safety concerns. If a single new lesion with >5 cm in any diameter develops, this was considered as a sign of toxicity.

No concerns as to Zenapax®-related adverse events arose during the course of these studies.

The study disclosed herein demonstrated the efficacy of Zenapax® therapy in subjects with multiple sclerosis by comparing the mean number of Gd-enhancing lesions during the pre-treatment period to that of the treatment period. The primary efficacy endpoint is the number of Gd-enhancing lesions.

The analyses on the primary endpoint included the following:
comparison of the mean number of lesions during the pre-treatment period (Weeks -8, -4, 0) to the mean number of lesions during the treatment period (Weeks 0 to 22)
comparison of the mean number of lesions during the pre-treatment period (Weeks -8, -4, 0) to the mean number of lesions during the last 12 weeks of the treatment period (Weeks 10-22)

These comparisons were performed using a paired t-test or the Wilcoxon signed rank test, depending on the distribution of the data. The means were based on non-missing evaluations.

This study also demonstrates the efficacy of Zenapax® therapy in subjects with multiple sclerosis using the following measures:
1. MRI measures
   T2 lesion load,
   Volume of Gd-enhancing lesions,
   Volume of T1 hypointensities (optional);
2. Clinical measures, specifically,
   Change in EDSS/SRS/9-hole peg test
   Relapse rate;
3. Immunologic measures, specifically,
   Markers of Th1 and Th2 T cell lineages, as well as FACS analysis of various T cell, B cell, and monocyte subset markers,
   Cytokine production by T cells in vitro T2 Lesion Load The analyses on T2 lesion load included the following:
comparison of the mean volume of T2 lesions during the pre-treatment period (Weeks -8, -4, 0) to the mean volume of T2 lesions during the treatment period (Weeks 0-22)
comparison of the mean volume of T2 lesions during the pre-treatment period (Weeks -8, -4, 0) to the mean volume of T2 lesions during the last 12 weeks of the treatment period (Weeks 10-22)

These comparisons were performed using a paired t-test or the Wilcoxon signed rank test, depending on the distribution of the data. The means were based on non-missing evaluations.

Volume of Gd-Enhancing Lesions

The analyses on volume of Gd-enhancing lesions included the following:
comparison of the mean volume of Gd-enhancing lesions during the pre-treatment period (Weeks -8, -4, 0) to the mean volume of Gd-enhancing lesions during the treatment period (Weeks 0-22)
comparison of the mean volume of Gd-enhancing lesions during the pre-treatment period (Weeks -8, -4, 0) to the mean volume of Gd-enhancing lesions during the last 12 weeks of the treatment period (Weeks 10-22)

These comparisons were performed using a paired t-test or the Wilcoxon signed rank test, depending on the distribution of the data. The means were based on non-missing evaluations.

Volume of T1 Hypointensities

The analyses on volume of T1 hypointensities included the following:
comparison of the mean volume of T1 hypointensities during the pre-treatment period (Weeks -8, -4, 0) to the mean volume of T1 hypointensities during the treatment period (Weeks 0-22)
comparison of the mean volume of T1 hypointensities during the pre-treatment period (Weeks -8, -4, 0) to the mean volume of T1 hypointensities during the last 12 weeks of the treatment period (Weeks 10-22)

These comparisons were performed using a paired t-test or the Wilcoxon signed rank test, depending on the distribution of the data. The means were based on non-missing evaluations.

EDSS

The change from baseline (Week 0) EDSS to Week 22 and Week 26 were determined. Also, change from baseline to week 22 and 26 for SRS and 9-hole peg test.

Relapses

The frequency of relapses over the 2 years prior to receiving study drug were compared to the frequency of relapses on study drug (Weeks 0 to 22).

Example 3

Outcome Measures: Immunologic Parameters

1. PBMC Cell Surface Expression Analyses

The analyses for the immunologic parameters were performed using standard methods. For example, parallel quantitative analysis of important markers for $Th_1/Th_2$ T cell development, effector functions of MS T cells and markers for the biological activity of the anti-Tac antibody with particular focus on T cell activation (i.e. determination IL-2 expression, numbers of $CD4^+$ and $CD3^+$ T cells expressing IL-2R/CD25; in vitro (proliferation to Tetanus toxoid; Flu-HA peptide 306-318) and in vivo (skin test) recall responses to standard recall antigens) were performed in treated subjects.

Specific studies included:
1. Analysis of changes in subpopulations of white blood cells (polymorphonuclear cells, monocytes, NK cells, LAK (lymphocyte-activated killer cells), lymphocytes—including B-cells, $CD4^+$ and $CD8^+$ subsets of T cells, NK-T cells, $CD4^+/CD25^+$ regulatory T cells) upon in vivo therapy with daclizumab
2. Evaluating the changes in surface expression of multiple activation markers, adhesion molecules, costimulatory molecules, cytokine- and chemokine receptors etc: CD95, CTLA-4, CD25 (IL-2Rα-chain), CD122 (IL-2Rβ-chain), CD132 (IL-2Rγ-chain),CD45RA, CD45RO, CD71, OX-40, CCR5, CXCR4, CD80, MHC-class II (HLA-DR, DQ, DP),TCR α/β, TCR γ/δ, CD2, CD56, CD161 by flow cytometry.
3. Evaluating proliferation of peripheral blood mononuclear cells (PBMC) to different polyclonal and antigen-specific stimuli (plate-bound anti-CD3, plate-bound anti-CD3+ anti-CD28, IL-2, IL-4, IL-7, IL-15, myelin basic protein (MBP), tetanus toxoid (TT) by flow-cytometry based proliferation assay using 5-(and- 6)-carboxyfluorescein diacetate, succinimidyl ester (5(6)-CFDA, SE). Cytokine production (i.e. IL-2, IL-4, IL-6, IL-8, IL-10, IL-12, IFN-γ, Tumor necrosis factor (TNF)-α, LT-α, transforming growth factor (TGF)-β) of PBMC stimulated with these various stimuli by sandwich ELISA 4. Longitudinal serum samples were collected from subjects in the trial to investigate the changes in antibody subtypes, myelin-specific antibodies, complement and complement-related markers, markers of oxidative stress and markers indicative of remyelination and repair.

The data obtained demonstrated that in vivo long-term administration of daclizumab leads to several immunoregulatory changes. Without being bound by theory, these changes likely contribute to the positive therapeutic effect of this drug in MS. The changes noted included:

Mild (~10%) decrease in total lymphocyte count (including CD4+ and CD8+ T cells and B-cells).

Concomitant increase in proportion of NK cells and NK-T cells—both of which were shown to have highly immunoregulatory activity in various animal models of autoimmunity and in human autoimmune disorders including MS, insulin dependent diabetes mellitus (IDDM) and systemic lupus erythematosus (SLE).

Upregulation of CD122 (IL-2R β-chain) on cell surface of NK cells, NK T cells and subpopulation of CD8+ lymphocytes that probably underlies increased proliferative capacity of these cells to IL-2 (via intermediate affinity IL-2R—i.e. CD122+CD132) and to IL-15 (which shares 2 signaling chains with IL-2R—i.e. CD 122 and CD132).

No significant decrease in proliferation of T cells (both CD4+ and CD8+ subsets) to strong polyclonal stimuli and to recall antigens like TT.

Increase of proliferation of NK cells, γ/δ-T cells, NK-T cells and subpopulation of CD8+ T cells to IL-15.

2. cDNA Microarray Expression Analyses

Daclizumab-induced immunomodulation upon long-term in-vivo administration in MS subjects was evaluated by cDNA microarrays performed on cryopreserved PBMC samples from baseline, treatment and post-treatment phase of clinical trial. The data obtained indicated that daclizumab therapy leads to upregulation of several genes of interest, including: suppressor of cytokine signaling 5 (SOCS5), jun-D-proto-oncogene, protein tyrosine phosphatase—receptor type, CD209-antigen-like, cell division cycle 14 (CDC14), CDC28-protein kinase regulatory subunit 2, and others. Daclizumab therapy also leads to down-modulation of several genes closely related to pro-inflammatory immunity, like IFN-γ and fibroblast growth factor 12 (FGF-12).

3. In vitro Functional Experiments

Studies of cryopreserved PBMC samples from subjects in clinical trial were performed in order to demonstrate in more detail the changes observed in longitudinal prospective samples and also add functional components to the observed structural changes:

a. Proliferation of PBMC was evaluated by flow-cytometry based proliferation assay using 5-(and-6)-carboxyfluorescein diacetate, succinimidyl ester (5(6)-CFDA, SE) to additional stimuli:

b. Plate-bound anti-CD3+ anti-CD28—as a potent polyclonal T-cell activating stimulus c. Keyhole limpet hemocyanin (KLH)—as an antigen for CD4+ T cells that humans are usually not exposed to, i.e. in order to investigate effect of daclizumab on naïve T cell priming d. Mixture of myelin antigens myelin basic protein (MBP) (146-170), PLP (139-154), MOG (35-55) and CNP (343-373)—in order to investigate effect of daclizumab on autoreactive T cells e. LPS—as a potent activator of monocytes and also CD4+/CD25+ regulatory T cells. In addition, PBMC were seeded with and without exogenous addition of daclizumab to demonstrate the differences between acute—in-vitro effects of daclizumab and prolonged—in vivo effects of daclizumab therapy. PBMC activated with these various stimuli were then transferred after 72h into IL-2 or IL-15 or IL-4-enriched media to observe whether observed upregulation of CD122 and CD132 on cell surface of these cells resulted in their increased functional response to cytokines that signal via these signaling molecules. Proliferation and cell expansion was measured at Day 6 and functional phenotype of these expanded cells was assessed by intracellular cytokine staining at Day 10 (measuring production of IL-2, IL-4, IL-6 and IFN-γ). In addition, supernatants were collected for evaluation of monocytes-producing cytokines and markers like IL-1β, IL-6, IL-10, TNF-α and NO.

f. Immunoregulatory properties of NK cells were assessed in more detail, e.g., NK T cells and CD4+/CD25+ T regulatory cells upon daclizumab therapy g. The gene expression profile from the cDNA microarray was verified by real-time PCR and by functional studies Results of these experiments indicate that:

The "acute" effects of in vitro daclizumab administration were different from prolonged effects of in vivo administration. More profound inhibition of T cell proliferation to various stimuli was noted acutely.

Standard doses of daclizumab (i.e. 1 mg/kg/4 weeks IV) were sufficient to block CD25 Tac epitope on T cells, but were were not sufficient to fully block CD25 on activated monocytes. Without being bound by theory, higher doses of daclizumab have been needed in many clinical situations (e.g. transplantation) due to insufficient block of CD25 by this dose. Hence, higher doses would be useful in very active subjects with autoimmune diseases.

CD25 epitope was blocked by daclizumab upon in vitro administration, but the molecule persists on cell surface of cells in same numbers. However, upon prolonged in vivo administration of daclizumab, this molecule is downmodulated from the cell surface of both CD4+ and CD8+ T cells.

Daclizumab administration influenced T cell priming: CD4+ T cells responding to naive antigen like KLH produce higher amounts of IL-4 and lower amounts of IFN-γ following daclizumab treatment. Without being bound by theory, the effect on T cell priming is believed to control the pro-inflammatory versus anti-inflammatory balance in MS and other autoimmune diseases.

Proliferation of T cells and their functional response to complementary cytokines sharing signaling chains with IL-2R (i.e. IL-15, IL-4, IL-7 and others) was enhanced upon daclizumab therapy.

Results also indicate monocyte activation is modulated upon daclizumab therapy as monocytes produced lower amounts of cytokines and had a greater response to IL-4.

Proliferation of CD4+/CD25+ T regulatory cells was enhanced upon daclizumab therapy (demonstrated with LPS, which stimulates this T cell subtype via Toll-4 receptor).

Example 4

Subject Assessment

The mean number of contrast-enhancing lesions between weeks 10-22 (3 months, 4 MRI scans) on combination therapy with weeks 42-62 (5 months, 6 MRI scans) on monotherapy was analyzed. Weeks 10-22 (3 months, 4 MRI scans) on combination therapy was compared with the entire time (weeks 24-62; 9 months and 10 MRI scans) on monotherapy.

The treatment response with single Zenapax® therapy was considered partial if a reduction of contrast-enhancing lesions from the baseline treatment, i.e. when subjects were on IFN-β alone, of >60% was not reached. If a reduction of contrast-enhancing lesions from baseline of >0, but <60% was reached, Zenapax® monotherapy was considered partially active. If disease activity returned to baseline levels, Zenapax® monotherapy was considered to have failed. However, none of these outcomes was detected.

Subjects entering the single therapy phase had lesion activity assessed monthly. The number of new lesions was evaluated following each monthly study. If the mean of lesion number over months 5, 6, 7 and 8 was 50% or less than the 3 months prior to entering monotherapy, efforts were made to continue the subjects on Zenapax® therapy until month 10 (week 62) on monotherapy (for one more year).

Figure 2:
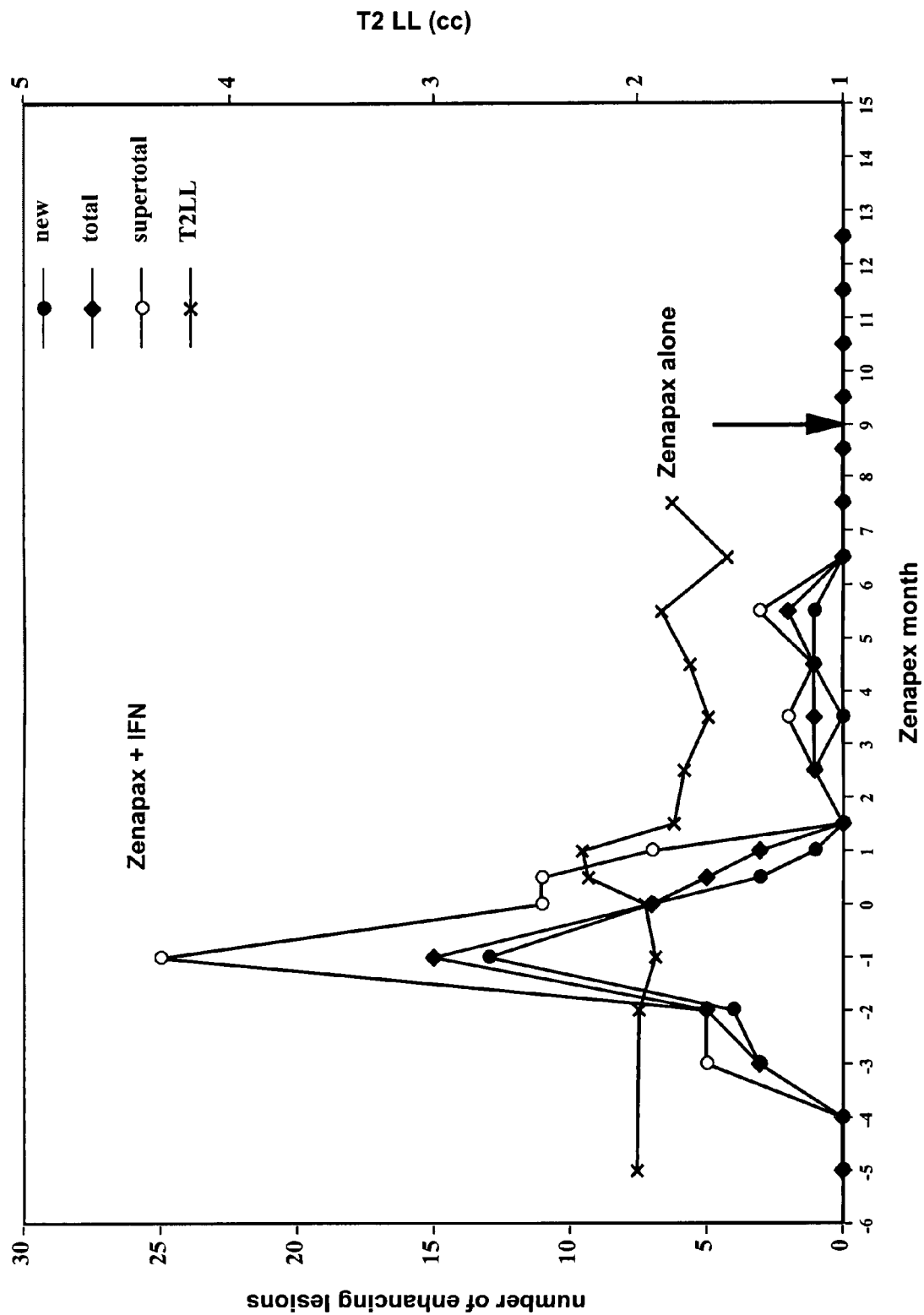
FIG. 2 is a graph of the number of new, total, supertotal and T2LL lesions in a second subject treated with Zenapax® alone over time. The subject did not respond to previous combination therapy with Zenapax® and interferon (IFN) beta, as indicated in the region to the right of the dashed vertical line. Initiation of Zenapax® monotherapy (in the absence of treatment with interferon-beta) is shown by the arrow. No new lesions were detected following the initiation of Zenapax® monotherapy.

Results from two subjects are shown in FIGS. 1 and 2. The number of new lesions was assessed by identifying on a single scan the number of brain lesions that were not previously identified. In addition the total number of lesions was assessed. These lesions included contrast enhancing lesions that persist for 1-2 months. Furthermore, the super-total number of lesions was assessed. These included lesions that appeared on more than one scan of the subject's brain, and provides an indirect measure of the lesion volume, i.e. via the appearance of one lesion on multiple MRI slices (supertotal of lesions).

As indicated in the FIGS. 1 and 2, treatment with Zenapax® alone (in the absence of IFN-β) resulted in a dramatic decrease in the number of total lesions. No new lesions were detected over a period of 5.5 months in any subject treated with Zenapax® alone (in the absence of IFN-β).

The data obtained during the last four months of treatment were compared to four months of baseline treatment. Thus, for each subject, the results obtained during the period of treatment with Zenapax® alone (in the absence of IFN-β) were compared to the results obtained during treatment with Zenapax® and IFN-β. New Gd lesion number was diminished by 85.95% (p=0.016). Total number of contrast enhancing lesions was decreased by 85.75% (p=0.004). The Gd lesion volume was reduced by 87% (p=0.014). The supertotal number of Gd enhancing lesions were reduced by 87.4% (p=0.008). The 9-hole peg test was reduced by 5.36% (p=0.004). The annualized relapse rate (number of relapses per subject per year) was reduced by 88.9% (p=0.047). The SRS was also reduced by 10.61% (p=0.035). All other measures improved by did not reach statistical significance. Thus, the primary outcome was significantly improved when the subjects were treated with Zenapax® alone.

Example 5

Dose Escalation

If subjects on the combination of IFN-β and Zenapax® showed a less than 75% reduction of disease activity compared to the baseline on IFN-β alone, their Zenapax® dose was increased to 2 mg/kg (monthly).

A subject entering the dose escalation was assessed after three months of therapy on the increased dose. No toxicity was noted over an 8.5 month trial period. The subject was treated with 2mg/kg of Zenapax® every other week (4 times the dose described above). The subject responded to Zenapax® therapy with a >60% reduction of contrast enhancing lesions.

Example 6

Combined Administration of IFN-β and Zenapax®

This example illustrates the effects of the combined administration of interferon-beta and an IL-2R antagonist in subjects having relapsing-remitting or secondary-progressive multiple sclerosis. The protocol is generally shown in Example 1, and is summarized below.

Inclusion Criteria

Subjects included in the trial were diagnosed with either relapsing-remitting or secondary-progressive multiple sclerosis; were between the ages of 16-65; scored between 1 and 6.5 on the EDSS; failed to respond to interferon-beta treatment alone as demonstrated by one or more exacerbations in the 18 months prior to enrollment, an increase of 1 point or more on the EDSS over 18 months of treatment, or persistence or reoccurrence of contrast enhancing lesions on brain MRI to at least one-half the mean of baseline monthly contrast enhancing lesions over a 6-month baseline period measured prior to the beginning of interferon-beta therapy; and must have had at least 3 gadolinium enhancing lesions in the first 3 pre-combination therapy MRI scans.

Exclusion Criteria

Subjects were excluded from the trial if they were diagnosed with primary-progressive MS; pre-treatment blood tests were abnormal; diagnosed with a concurrent clinically significant major disease; contraindications to monoclonal antibody therapies were observed; determined to be positive for HIV; treated with glatiramer acetate or cyclophosphamide in the 26 weeks prior to the trial, or treated with intravenous immunoglobulin (IVIg), azathioprine (AZA), methotrexate (MTX), cyclosporin, cyclophosphamide (CTC), cladribine, or mitox in the 12 weeks prior to the trial, or treated with corticosteroids or adrenocorticotrophic hormone (ACTH) in the 8 weeks prior to the trial, or treated with any other investigational drug or procedure for MS; not practicing adequate contraception; or breastfeeding.

Course of Treatment

Ten subjects (one additional one under the abovementioned single subject exemption with a higher dose) participated in the trial of the combination therapy. For each subject a baseline 3-month period of treatment with interferon-beta (Avonex® or Betaseron®) was established. Avonex® was administered as indicated in the prescribing information supplied by the manufacturer at a dose of 30 µg injected intramuscularly once a week. Betaseron® was administered as indicated in the prescribing information supplied by the manufacturer at a dose of 0.25 mg injected subcutaneously every other day. Four MRI scans were performed during the baseline period to determine a baseline number of contrast enhancing lesions, one at the beginning of the period and then at the end of each month of the baseline period with the fourth just prior to the beginning of the combination therapy. Subjects were also evaluated on the EDSS, the Scripps Neurologic Rating Scale (NRS), and various ambulation and other motor skill tests.

Combined therapy began after the 3-month baseline was established. Interferon-beta treatment was continued and, in addition, anti-Tac (Zenapax®) was administered for 5.5 months. During the first month of the combined administration Zenapax® was administered every other week and thereafter Zenapax® was administered once a month. Zenapax® was administered intravenously in the manner described in the manufacturer's prescribing information at a dose of 1 mg/kg of body weight. One subject received a dose of 2 mg/kg every other week after showing no response to the 1 mg/kg dose. MRI scans were performed during the combined treatment period to determine changes in the number of contrast enhancing lesions, one every two weeks for the first six weeks of treatment, and thereafter monthly for a total of 8 MRI scans. On the same schedule subjects were also evaluated on the EDSS, the Scripps NRS, and various ambulation and other motor skill tests.

Results

Figure 3:
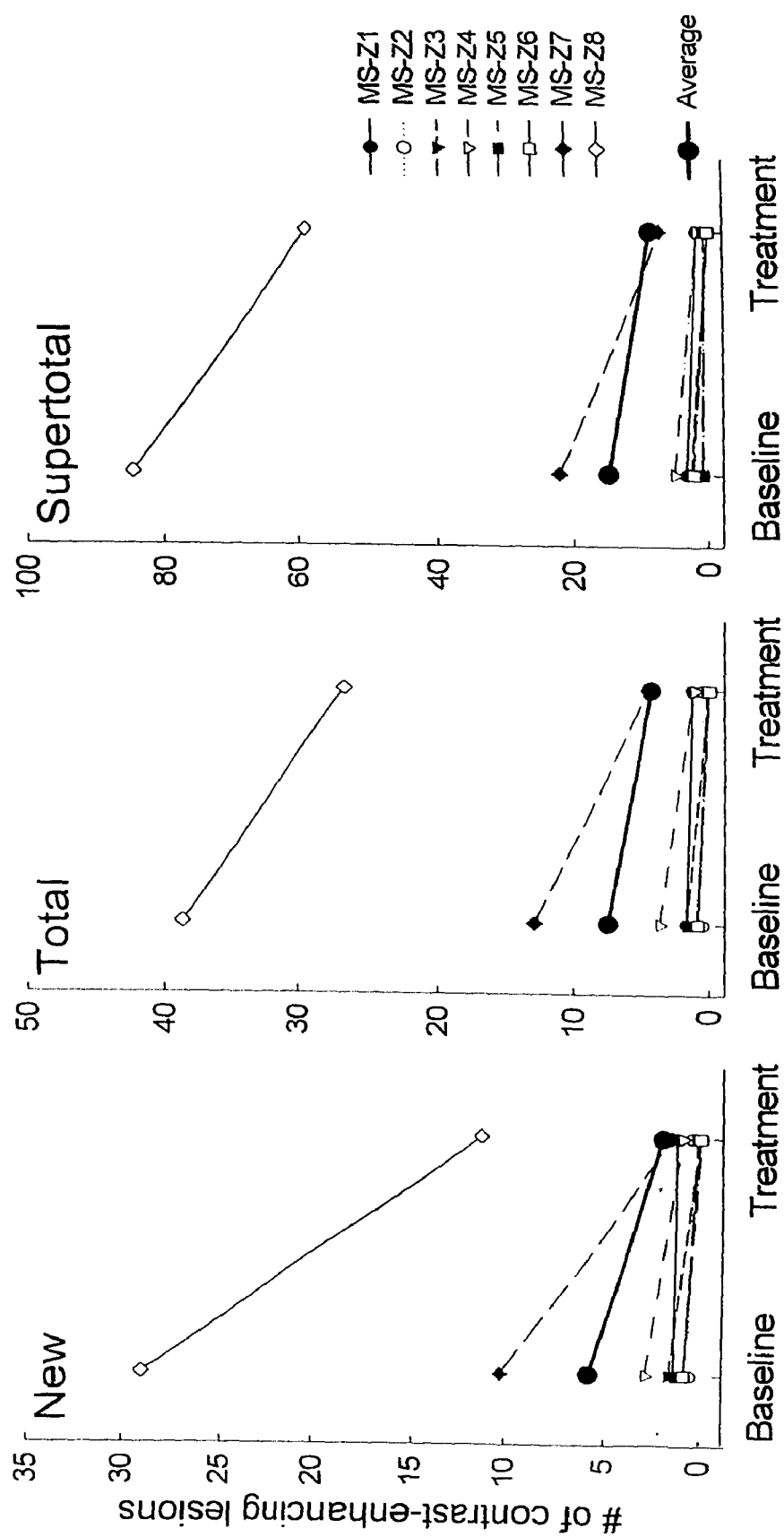
FIG. 3 is a set of graphs showing the changes in new, total and supertotal contrast enhancing lesions as measured by magnetic resonance imaging (MRI) scans in subjects treated with a combination of daclizumab and interferon-beta showing the difference between a 3-month baseline period of treatment only with interferon-beta and after combination therapy in eight subjects.
Figures 4A, 4B:
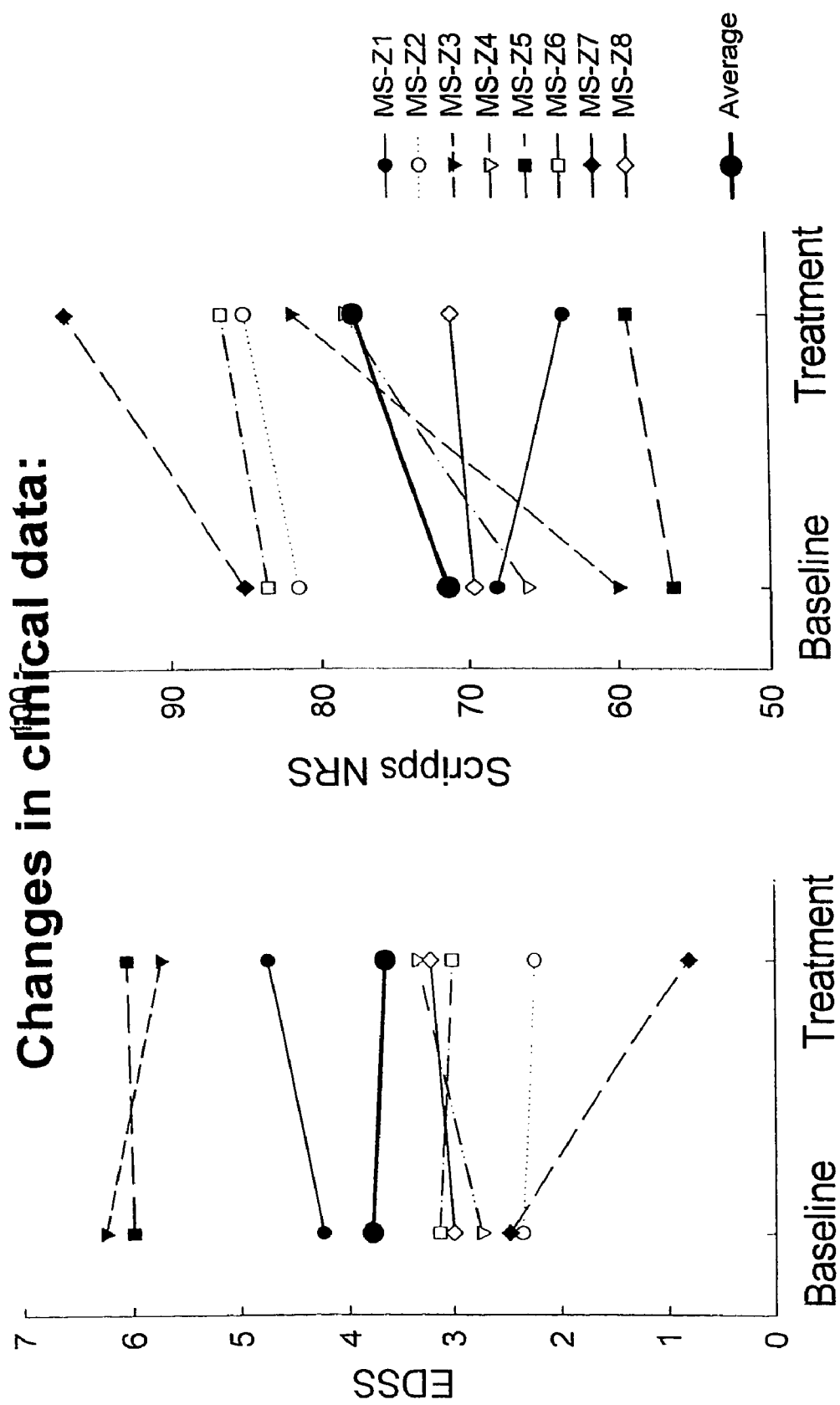
FIGS. 4A and 4B are graphs showing changes in neurological performance as measured by performance on the Expanded Disability Status Scale (EDSS) (FIG. 4A) and the Scripps Neurologic Rating Scale (NRS) (FIG. 4B) between the baseline period and after combination therapy for the same subjects as in FIG. 3.
Figures 5A, 5B:
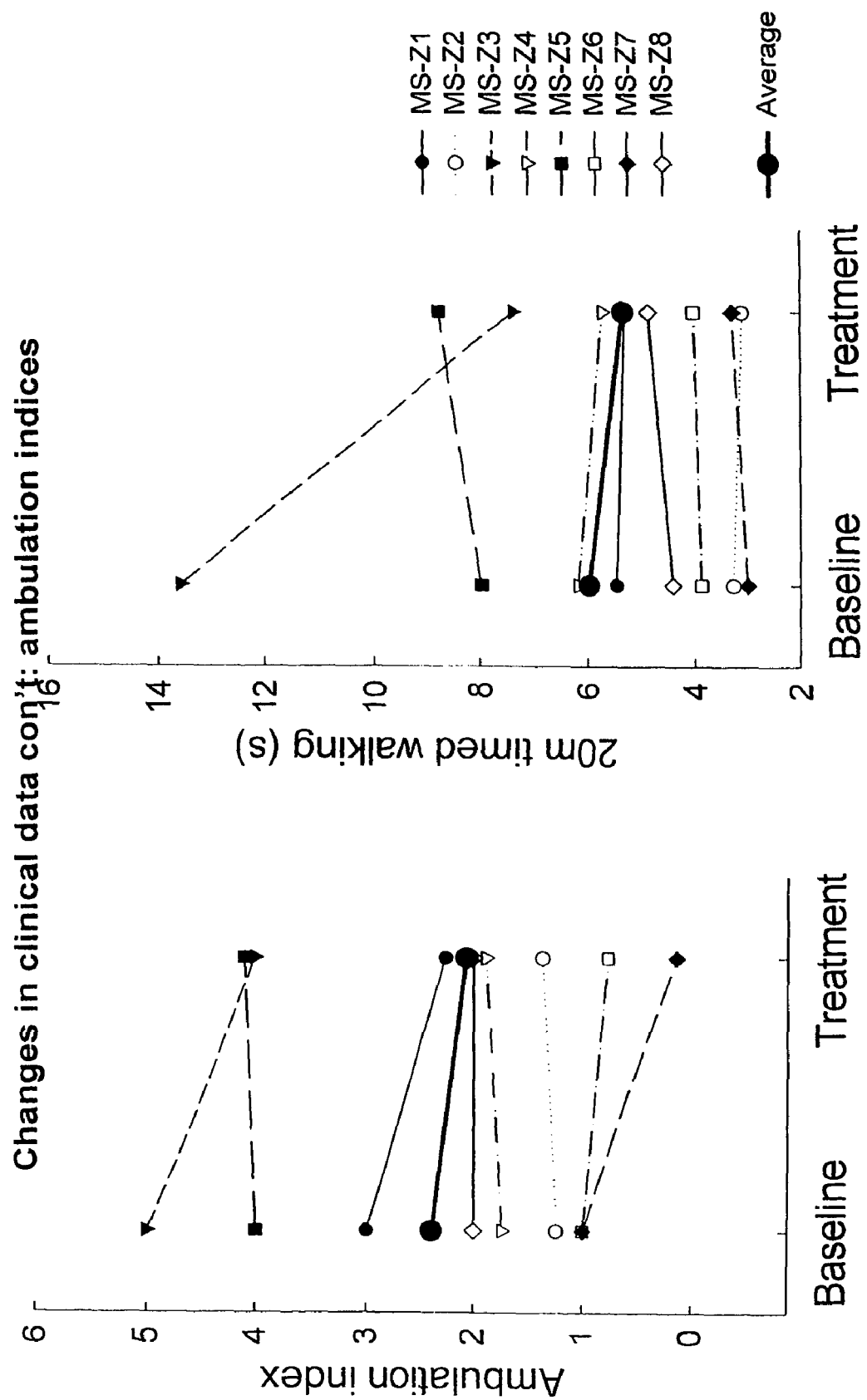
FIGS. 5A and 5B are graphs showing changes in neurological performance as measured by performance on the ambulation index (FIG. 5A) and the timed 20 m walk (FIG. 5B) between the baseline period and after combination therapy for the same subjects as in FIG. 3.
Figures 6A, 6B:
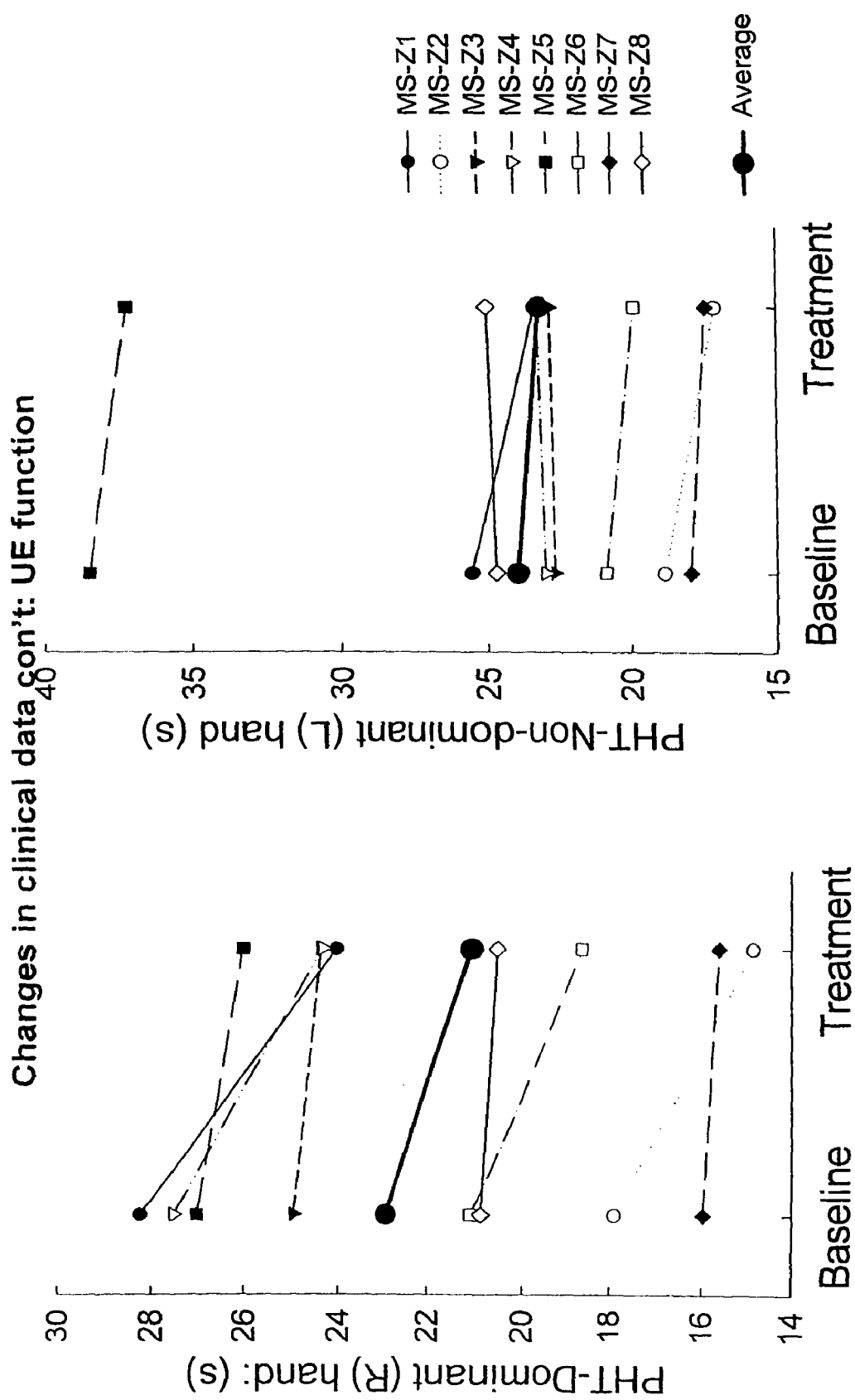
FIGS. 6A and 6B are graphs showing changes in neurological performance as measured by the 9-peg hole test times for dominant (FIG. 6A) and non-dominant (FIG. 6B) hands respectively, between the baseline period and after combination therapy for the same subjects as in FIG. 1.

The combined administration of interferon-beta and Zenapax® led to almost complete cessation of disease activity and clinical improvement in seven of eight subjects. As can be seen in FIG. 3, seven of eight subjects had either fewer or at least no increase in both new and total contrast enhancing lesions under the combination therapy as compared to the baseline period. As shown in FIG. 4A, four of eight subjects also demonstrated improvement on the EDSS under the combination therapy as compared to the baseline period. As shown in FIG. 4B, seven of eight subjects demonstrated improvement on the Scripps NRS. Referring to FIG. 4A, five of eight subjects demonstrated improved ambulation on the ambulation index. As shown in FIG. 5B, five of eight subjects either improved or had no change in a timed 20 m walk. As shown in FIG. 6A, all subjects demonstrated improved times with their dominant hand on the peg hole test. As shown in FIG. 6B, five of eight subjects also improved with their non-dominant hand on the peg hole test.

Example 7

Effects on T Cells in Combination Therapy

This example demonstrates the saturation of the Tac epitope following combination therapy and the parallel decrease in T-cell proliferation as compared to the baseline period.

Figure 7:
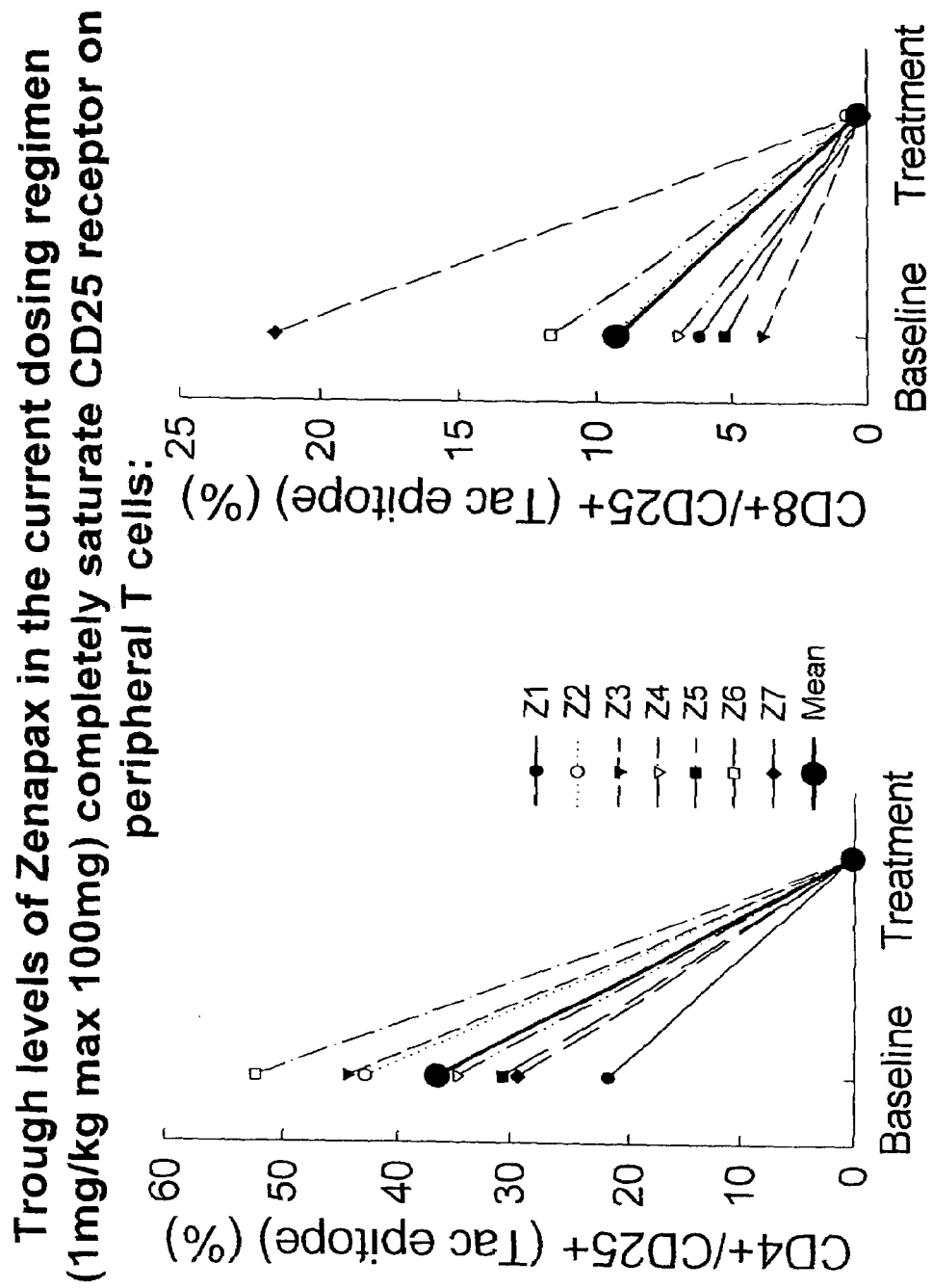
FIG. 7 is a set of graphs showing changes in the percentage of CD4+/CD25+ cells and CD8+/CD25+ cells expressing the Tac epitope between the baseline period and after combination therapy for seven of the subjects from FIG. 3.

Saturation of the Tac epitope was studied by flow cytometry. The combined administration of interferon-beta with 1 mg/kg of Zenapax® caused complete saturation of the Tac epitope on CD4+/CD25+ and CD8+/CD25+ T-cells (FIG. 7).

Figure 8:
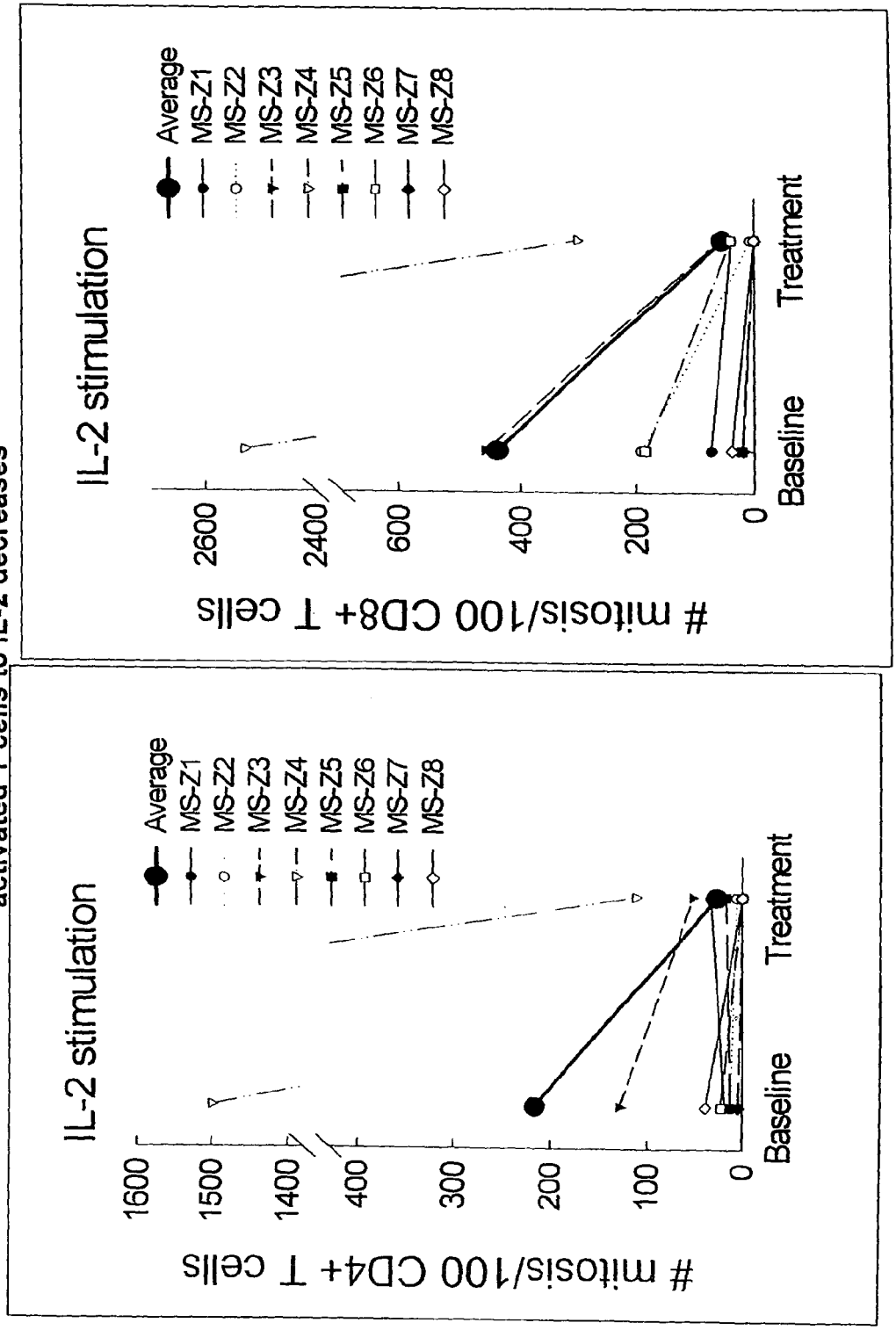
FIGS. 8A and 8B are graphs showing changes in the number of CD4 T cell mitoses per one-hundred cells (FIG. 8A) and CD8 T cell mitoses per one-hundred cells (FIG. 8B) between the baseline period and after combination therapy for the same subjects as in FIG. 3.

Proliferation of activated T-cells was measured by carboxyfluorescein succinimidyl ester (CFSE) fluorescence cell labeling and assessing the number of mitoses in CFSE-labeled cells by flow cytometry. As shown in FIG. 8A, six of eight subjects demonstrated decreased proliferation of CD4 T-cells. Referring to FIG. 8B, all subjects demonstrated a decrease in the proliferation of CD8 T cells as compared to the baseline period.

Example 8

Upregulation of CTLA-4

This example demonstrates the unexpected upregulation of CTLA-4 caused by the combined administration of interferon-beta and an IL-2R antagonist.

CLTA-4 surface expression was measured by utilizing antibodies against CTLA-4 and flow cytometry. For each measurement of CTLA-4 surface expression, first, a 5 milliliter (ml) tube of whole blood in ethylene diamine tetraacetic acid (EDTA) was obtained from each subject. Then, 42 ml of 1× lysing solution (4.2 ml 10 lysing solution +37.8 ml $H_2O$) was prepared from 10× stock prepared by dissolving in 1 liter of distilled water: 89.9 g $NH_4Cl$, 10.0 g KHCO3, 370.0 mg tetrasodium EDTA; and adjusting the solution to pH 7.3. 3 ml of blood was transferred by pipette into the 42 ml of 1× lysing solution (in 50 ml Falcon tubes). The mixture was allowed to stand at room temperature for 3-5 minutes. It was then centrifuged at 300× gravity for 5 minutes at room temperature. The supernatant was aspirated and the pellet was resuspended in 30 ml of cold X-vivo media. The resuspended mixture was centrifuged at 300× gravity for 5 minutes at 2-8° C., the supernatant was aspirated, and the pellet was resuspended in 2.5 ml of protein-enriched phosphate buffered saline (PBS) (10 ml of fetal calf serum (FCS) in 500 ml of 1×PBS). This cell suspension was divided into 200 µl aliquots in a 96 well plate, then centrifuged at 300× gravity for 5 minutes. The supernatant was discarded. Staining was performed by adding 10 microliter (µl)/well of prepared anti-CTLA-4 antibody mixture. The plate was then incubated for 30 minutes on ice in a dark container. Each well was washed with 200 µl of cold wash-buffer—mixed gently, and spun at 1000 rpm. Supernatants were removed and each well washed another 2 times with 200 µl of wash-buffer. After the last wash, the pellet was resuspended in 200 µl of staining buffer and analyzed by Fluorescence-Activated Cell Sorter (FACS)-Calibur. At least 10000 events gated on lymphocytes and 5000 events gated on monocytes were acquired.

Figure 9:
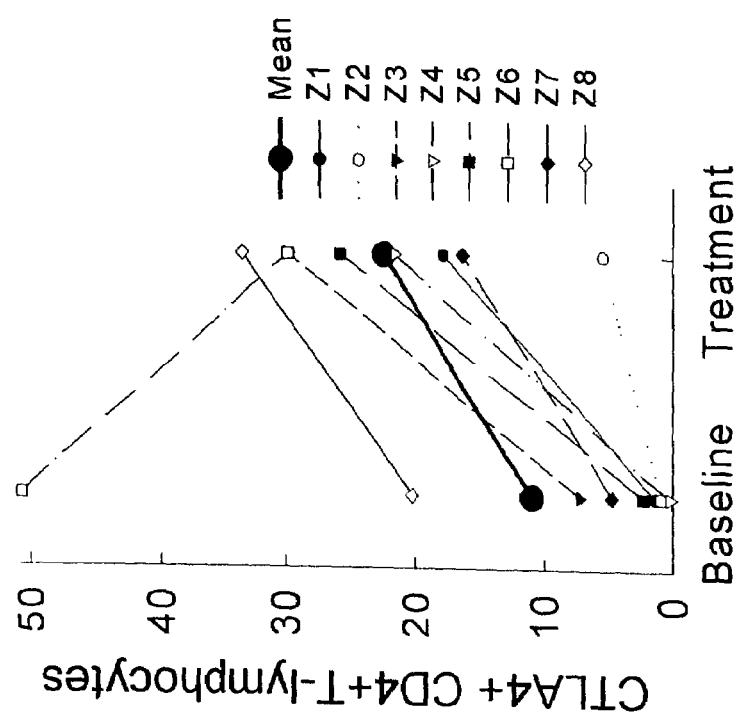
FIG. 9 is a graph showing changes in the number of CD4 T cells expressing cytotoxic T lymphocyte-associated antigen 4 (CTLA-4) on their surface as measured by fluorescence-activated cell sorting of blood samples between the baseline period and after combination therapy for the same subjects as in FIG. 3.

As shown in FIG. 9, seven of eight subjects demonstrated significant upregulation of CTLA-4 during the combined therapy as compared to the baseline period.

It will be apparent that the precise details of the methods or compositions described may be varied or modified without departing from the spirit of the described invention. We claim all such modifications and variations that fall within the scope and spirit of the claims below.

The invention claimed is:

1. A method for treating a subject with multiple sclerosis, comprising administering to the subject a therapeutically effective amount of daclizumab, in the absence of treatment with beta interferon, wherein the subject has failed to respond to previous treatment with beta interferon, thereby ameliorating a symptom of multiple sclerosis and treating the subject.

2. The method of claim 1, wherein daclizumab is administered intravenously.

3. The method of claim 1, wherein daclizumab is administered at a dose of about 1 to about 3 milligrams per kilogram intravenously.

4. The method of claim 1, wherein daclizumab is administered at a dose of about 1 per kilogram to about 2 milligrams per kilogram intravenously.

5. The method of claim 1, wherein daclizumab is administered biweekly.

6. The method of claim 1, wherein treatment of the subject results in a decreased number of contrast enhancing-lesions as evaluated by Magnetic Resonance Imaging.

7. The method of claim 1, wherein the subject has failed to respond to treatment with interferon-beta 1a.

8. The method of claim 1, wherein the subject has failed to respond to treatment with interferon-beta 1b.

9. The method of claim 1, wherein the subject has relapsing-remitting multiple sclerosis.

10. The method of claim 1, wherein the subject has secondary progressive multiple sclerosis.

11. The method of claim 1, wherein daclizumab is administered at least biweekly for a period of at least two months, thereby treating the subject.

12. The method of claim 11, wherein the antibody is administered at a dose of about 1 to about 3 milligrams per kilogram.

13. The method of claim 11, wherein the antibody is administered at a dose of about 1 milligram per kilogram to about 2 milligrams per kilogram.

14. The method of claim 11, wherein the subject has relapsing-remitting multiple sclerosis.

15. A method for treating a subject with multiple sclerosis, comprising selecting a subject with relapsing remitting multiple sclerosis who has been treated with interferon-beta and failed to respond to the interferon-beta treatment; administering to the subject intravenously a therapeutically effective amount of daclizumab wherein the subject is not treated with interferon-$\beta$, thereby ameliorating a symptom of multiple sclerosis and treating the subject.

16. The method of claim 15, wherein daclizumab is administered at least biweekly for a period of at least two months.

17. The method of claim 1, wherein daclizumab administered subcutaneously.

* * * * *

UNITED STATES PATENT AND TRADEMARK OFFICE
CERTIFICATE OF CORRECTION

PATENT NO. : 7,258,859 B2
APPLICATION NO. : 10/607598
DATED : August 21, 2007
INVENTOR(S) : Roland Martin, Henry McFarland and Bibiana Bielekova It is certified that error appears in the above-identified patent and that said Letters Patent is hereby corrected as shown below:

On the Title Page

Column 1, Item (60), add the following:

-- Continuation-in-part of application No. PCT/US02/38290, filed Nov. 27, 2002. --

In the Speciation

Column 1, lines 6-9 should read as follows:

-- This application claims priority under 35 U.S.C. 365(c) to, and is continuation-in-part of, PCT Application No. PCT/US02/38290, filed Nov. 27, 2002, which claims the benefit of U.S. Provisional Application No. 60/393,021, filed Jun. 28, 2002. The prior applications all are incorporated by reference in their entirety. --

Signed and Sealed this
Sixteenth Day of December, 2014

Michelle K. Lee
*Deputy Director of the United States Patent and Trademark Office*